United States Patent
Bermond et al.

(10) Patent No.: US 12,011,454 B2
(45) Date of Patent: Jun. 18, 2024

(54) NICOTINAMIDE MONONUCLEOTIDE DERIVATIVES AND USE THEREOF IN THE TREATMENT AND PREVENTION OF A RED BLOOD CELL DISORDER

(71) Applicant: Nuvamid SA, Epalinges (CH)

(72) Inventors: Guillaume Bermond, Epalinges (CH); Laurent Garçon, Velaux (FR); Matthias Canault, Velaux (FR); Cecile Cros, Epalinges (CH)

(73) Assignee: NUVAMID SA, Epalinges (CH)

( * ) Notice: Subject to any disclaimer, the term of this patent is extended or adjusted under 35 U.S.C. 154(b) by 0 days.

(21) Appl. No.: 18/221,516

(22) Filed: Jul. 13, 2023

(65) Prior Publication Data

US 2023/0355650 A1   Nov. 9, 2023

Related U.S. Application Data

(63) Continuation of application No. 18/028,080, filed as application No. PCT/EP2021/086437 on Dec. 17, 2021.

(30) Foreign Application Priority Data

Dec. 18, 2020  (EP) ..................... 20215833

(51) Int. Cl.
  *A61K 31/706*  (2006.01)
  *A61K 31/198*  (2006.01)
  *A61P 7/06*  (2006.01)

(52) U.S. Cl.
  CPC .......... *A61K 31/706* (2013.01); *A61K 31/198* (2013.01); *A61P 7/06* (2018.01)

(58) Field of Classification Search
  None
  See application file for complete search history.

(56) References Cited

U.S. PATENT DOCUMENTS 7,776,326 B2 *  8/2010  Milbrandt ................ A61P 3/02
424/94.5

FOREIGN PATENT DOCUMENTS

| WO | WO-2006/105440 A2 | 10/2006 |
| WO | WO-2007/008548 A2 | 1/2007 |
| WO | WO-2015/186114 A1 | 12/2015 |

OTHER PUBLICATIONS

Griesshammer, Martin, Heinz Gisslinger, and Ruben Mesa. "Current and future treatment options for polycythemia vera." Annals of hematology 94 (2015): 901-910.*
Paton D M et al., "Mechanism of Presynaptic Inhibition of Cholinergic Transmission In Guinea-Pig Ileum by Adenine Nucleotides", Methods and Findings In Experimental and Clinical Pharmacology, vol. 7, No. 2, 1985, pp. 65-68, XP009527753, ISSN: 0379-0355, abstract.
International Search Report and Written Opinion of the International Searching Authority, issued in PCT/EP2021/086437, dated Mar. 29, 2022; ISA/EP.

* cited by examiner

*Primary Examiner* — Patrick T Lewis
(74) *Attorney, Agent, or Firm* — Harness Dickey & Pierce PLC

(57) ABSTRACT

The present invention relates to nicotinamide mononucleotide derivatives of Formula (I)

for use in the treatment and/or prevention of a blood disorder, especially sickle cell disease. The present invention further relates to pharmaceutical compositions comprising compounds of Formula (I) for use in the treatment and/or prevention of a red blood cell disorder, especially sickle cell disease.

16 Claims, 4 Drawing Sheets

NICOTINAMIDE MONONUCLEOTIDE DERIVATIVES AND USE THEREOF IN THE TREATMENT AND PREVENTION OF A RED BLOOD CELL DISORDER

FIELD OF INVENTION

The present invention relates to nicotinamide mononucleotide derivatives compounds for use in the treatment and/or prevention of a red blood cell disorder.

BACKGROUND OF INVENTION

A blood disorder is a condition affecting blood cells such as red blood cells, white blood cells, or the smaller circulating cells called platelets, which are critical for clot formation. All three cell types form in the bone marrow, which is the soft tissue inside the bones. Red blood cells transport oxygen to the body's organs and tissues. White blood cells help the body fight infections. Platelets help the blood to clot. Blood cell disorders impair the formation and function of one or more of these types of blood cells.

Among blood disorders, sickle cell disease (SCD) or drepanocytosis is a group of inherited red blood cell disorders defined by a missense point mutation in the sequence of beta globin, which results in a glutamic acid residue at position 6 being substituted by a valine. This mutated globin, called sickle hemoglobin or hemoglobin S (HbS), aggregates and forms fibrous precipitates upon low oxygen level, leading to polymerized hemoglobin and promoting red blood cell (RBC) sickling.

Clinical manifestations of SCD derive from at least three different pathophysiologic mechanisms: the loss of deformability of the RBC leading to vascular obstruction and ischemia; a shortened lifespan of the RBC leading to both intravascular and extravascular hemolysis; a sticky RBC surface increasing adherence to the vascular endothelium which can result in vascular obstruction and can contribute to vascular proliferative lesions.

Recurrent acute pain crises, or vaso-occlusive crises (VOCs) are considered among the most common manifestations of SCD. VOCs are believed to occur when blood flow is obstructed, usually at the level of the small blood vessels resulting in ischemic injury and pain.

Over time patients will also experience significant acute and chronic complications. Acute complications include serious infections such as meningitis, osteomyelitis, and sepsis, and noninfectious complications such as stroke, renal necrosis, priapism. Acute chest syndrome is a potentially life-threatening complication that can involve chest pain and shortness of breath among other symptoms; some episodes of acute chest syndrome are triggered by infection. Chronic complications can emerge across multiple organs and include neurocognitive impairment, chronic kidney injury, delayed puberty, avascular necrosis, retinopathy, pulmonary hypertension, skin ulcers, and chronic pain. Individuals with SCD face ongoing and evolving lifelong difficulties as a result of their disease.

SCD affects over 5 million subjects in the world, being the most common genetic disease in France. Despite the recent advances in the field, therapy for SCD patients is limited to symptomatic treatment of pain, oxygen supplementation, antibiotics, RBC transfusions and hydroxyurea. Nonetheless, blood transfusion remains the most applied therapy to treat patients suffering from SCD.

Alternative approaches, such as bone marrow transplantation and gene therapy have been developed but are still associated with toxicity and are only considered in case of cerebral vasculopathy. Moreover, these approaches are not yet feasible in most countries where the incidence of the disease is elevated.

Oxidative stress contributes to the complex pathophysiology of sickle cell disease. Nicotinamide adenine dinucleotide (NAD+) is a ubiquitous oxidation-reduction (redox) cofactor in red cells. NAD+ and its reduced form, NADH, play major roles in maintaining redox balance. Sickle red cells have a lower redox ratio ([NADH]:[NAD++NADH]) than normal red cells.

The amino acid L-glutamine (USAN, glutamine) is required to synthesize NAD. Uptake of L-glutamine is several times greater in sickle red cells than in normal red cells, primarily to increase the total intracellular NAD level. Oral administration of pharmaceutical-grade L-glutamine was shown to raise the NAD redox ratio within sickle cells and was associated with patient-reported clinical improvement.

A phase 3 trial of L-glutamine in SCD showed that the median number of pain crises over 48 weeks was lower among the patients who received L-glutamine. On the basis of the results of this phase 3 trial, the FDA granted approval of pharmaceutical grade L-glutamine (Endari, Emmaus Medical) as a prescription drug to reduce the rate of acute complications of sickle cell disease among adults and children 5 years of age and older.

Some other protocols have recently been granted by the FDA to treat SCD or reduce complications associated with SCD: Voxelotor (Oxbryta™), which inhibits polymerization of HbS by promoting the binding of oxygen to hemoglobin, has been approved to treat SCD in adults and children 12 years of age and older; and Crizanlizumab (Adakveo™), a therapeutic monoclonal antibody that reduces the phenomenon of cell aggregation during VOCs by inhibiting P-Selectin, a cell adhesion molecule, has been approved in adults and children 16 years of age and older.

However, while current treatments have greatly increased the life expectancy of affected patients, they are still limited as the effectiveness of these drugs varies depending on the patient and the clinical manifestation observed. Moreover, further studies need to be done to assess whether the beneficial effect observed on SCD complications is preserved over the years.

Therefore, the research for new therapeutic targets to treat SCD and complications associated with SCD is of great importance.

The purpose of the present invention is thus to provide a safe prophylactic and/or therapeutic treatment of a red blood cell disorder, particularly of sickle cell disease, by providing nicotinamide mononucleotide or derivatives thereof for use in the treatment and/or prevention of sickle cell disease.

The Applicant surprisingly found that the nicotinamide mononucleotide derivatives according to the invention are potent agents to treat and/or prevent a red blood cell disorder, particularly sickle cell disease, and/or complications associated with said red blood cell disorder, particularly sickle cell disease, and are well tolerated.

SUMMARY

This invention thus relates to a compound of Formula (I),

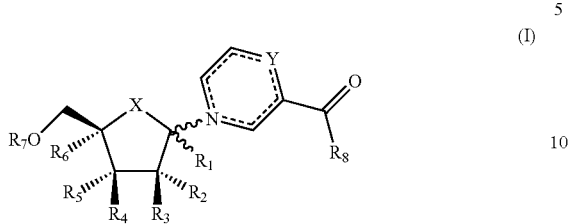

(I)

or a pharmaceutically acceptable salt or solvate thereof; wherein:

X is selected from O, $CH_2$, S, Se, CHF, $CF_2$ and $C=CH_2$;

$R_1$ is selected from H, azido, cyano, $(C_1-C_8)$alkyl, $(C_1-C_8)$thio-alkyl, $(C_1-C_8)$heteroalkyl and OR; wherein R is selected from H and $(C_1-C_8)$alkyl;

$R_2$, $R_3$, $R_4$ and $R_5$ are independently selected from H, halogen, azido, cyano, hydroxyl, $(C_1-C_{12})$alkyl, $(C_1-C_{12})$thio-alkyl, $(C_1-C_{12})$heteroalkyl, $(C_1-C_{12})$haloalkyl and OR; wherein R is selected from H, $(C_1-C_{12})$alkyl, —C(O)$(C_1-C_{12})$alkyl, —C(O)NH$(C_1-C_{12})$alkyl, —C(O)O$(C_1-C_{12})$alkyl, —C(O)aryl, —C(O)$(C_1-C_{12})$alkyl-$(C_5-C_{12})$aryl, —C(O)NH$(C_1-C_{12})$alkyl-$(C_5-C_{12})$aryl, —C(O)O$(C_1-C_{12})$alkyl-$(C_5-C_{12})$aryl and —C(O)CHR$_{AA}$NH$_2$; wherein R$_{AA}$ is a side chain selected from a proteinogenic amino acid;

$R_6$ is selected from H, azido, cyano, $(C_1-C_8)$alkyl, $(C_1-C_8)$thio-alkyl, $(C_1-C_8)$heteroalkyl and OR; wherein R is selected from H and $(C_1-C_8)$alkyl;

$R_7$ is selected from P(O)$R_9R_{10}$, P(S)$R_9R_{10}$ and

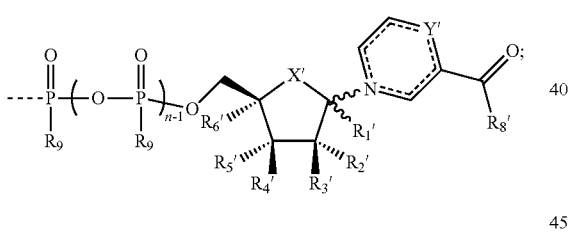

wherein:

$R_9$ and $R_{10}$ are independently selected from OH, $OR_{11}$, $NR_{13}R_{14}$, $(C_1-C_8)$alkyl, $(C_2-C_8)$alkenyl, $(C_2-C_8)$alkynyl, $(C_3-C_{10})$cycloalkyl, $(C_5-C_{12})$aryl, $(C_5-C_{12})$aryl-$(C_1-C_8)$alkyl, $(C_1-C_8)$alkyl-$(C_5-C_{12})$aryl, $(C_1-C_8)$heteroalkyl, $(C_3-C_8)$heterocycloalkyl, $(C_5-C_{12})$heteroaryl and NHCR$_\alpha$R$_{\alpha'}$C(O)OR$_{12}$; wherein:

$R_{11}$ is selected from $(C_1-C_{10})$alkyl, $(C_3-C_{10})$cycloalkyl, $(C_5-C_{12})$aryl, $(C_1-C_{10})$alkyl-$(C_5-C_{12})$aryl, substituted $(C_5-C_{12})$aryl, $(C_1-C_{10})$heteroalkyl, $(C_1-C_{10})$haloalkyl, —(CH$_2)_m$C(O)$(C_1-C_{15})$alkyl, —(CH$_2)_m$OC(O)$(C_1-C_{15})$alkyl, —(CH$_2)_m$OC(O)O$(C_1-C_{15})$alkyl, —(CH$_2)_m$SC(O)$(C_1-C_{15})$alkyl, —(CH$_2)_m$C(O)O$(C_1-C_{15})$alkyl, —(CH$_2)_m$C(O)O$(C_1-C_{15})$alkyl-$(C_5-C_{12})$aryl; wherein m is an integer selected from 1 to 8; and —P(O)(OH)OP(O)(OH)$_2$; and an internal or external counterion;

$R_{12}$ is selected from hydrogen, $(C_1-C_{10})$alkyl, $(C_2-C_8)$alkenyl, $(C_2-C_8)$alkynyl, $(C_1-C_{10})$haloalkyl, $(C_3-C_{10})$cycloalkyl, $(C_3-C_{10})$heterocycloalkyl, $(C_5-C_{12})$aryl, $(C_1-C_4)$alkyl-$(C_5-C_{12})$aryl and $(C_5-C_{12})$heteroaryl; wherein said aryl or heteroaryl groups are optionally substituted by one or two groups selected from halogen, trifluoromethyl, $(C_1-C_6)$alkyl, $(C_1-C_6)$alkoxy and cyano;

$R_{13}$ and $R_{14}$ are independently selected from H, $(C_1-C_8)$alkyl and $(C_1-C_8)$alkyl-$(C_5-C_{12})$aryl; and $R_\alpha$ and $R_{\alpha'}$ are independently selected from an hydrogen, $(C_1-C_{10})$alkyl, $(C_2-C_{10})$alkenyl, $(C_2-C_{10})$alkynyl, $(C_3-C_{10})$cycloalkyl, $(C_1-C_{10})$thio-alkyl, $(C_1-C_{10})$hydroxyalkyl, $(C_1-C_{10})$alkyl-$(C_5-C_{12})$aryl, $(C_5-C_{12})$aryl, —(CH$_2)_3$NHC(=NH)NH$_2$, (1H-indol-3-yl)methyl, (1H-imidazol-4-yl)methyl and a side chain selected from a proteinogenic or non-proteinogenic amino acid; wherein said aryl groups are optionally substituted with a group selected from hydroxyl, $(C_1-C_{10})$alkyl, $(C_1-C_6)$alkoxy, halogen, nitro and cyano; or $R_9$ and $R_{10}$ together with the phosphorus atom to which they are attached form a 6-membered ring wherein —$R_9$—$R_{10}$— represents —O—CH$_2$—CH$_2$—CHR—O—; wherein R is selected from hydrogen, $(C_5-C_6)$aryl and $(C_5-C_6)$heteroaryl; wherein said aryl or heteroaryl groups are optionally substituted by one or two groups selected from halogen, trifluoromethyl, $(C_1-C_6)$alkyl, $(C_1-C_6)$alkoxy and cyano;

X' is selected from O, $CH_2$, S, Se, CHF, $CF_2$ and $C=CH_2$;

$R_{1'}$ is selected from H, azido, cyano, $(C_1-C_8)$alkyl, $(C_1-C_8)$thio-alkyl, $(C_1-C_8)$heteroalkyl and OR; wherein R is selected from H and $(C_1-C_8)$alkyl; $R_{2'}$, $R_{3'}$, $R_{4'}$ and R, are independently selected from H, halogen, azido, cyano, hydroxyl, $(C_1-C_{12})$alkyl, $(C_1-C_{12})$thio-alkyl, $(C_1-C_{12})$heteroalkyl, $(C_1-C_{12})$haloalkyl and OR; wherein R is selected from H, $(C_1-C_{12})$alkyl, —C(O)$(C_1-C_{12})$alkyl, —C(O)NH$(C_1-C_{12})$alkyl, —C(O)O$(C_1-C_{12})$alkyl, —C(O)aryl, —C(O)$(C_1-C_{12})$alkyl-$(C_5-C_{12})$aryl, —C(O)NH$(C_1-C_{12})$alkyl-$(C_5-C_{12})$aryl, —C(O)O$(C_1-C_{12})$alkyl-$C_5-C_{12}$aryl and —C(O)CHR$_{AA}$NH$_2$; wherein R$_{AA}$ is a side chain selected from a proteinogenic amino acid;

$R_{6'}$ is selected from H, azido, cyano, $(C_1-C_8)$alkyl, $(C_1-C_8)$thio-alkyl, $(C_1-C_8)$heteroalkyl and OR; wherein R is selected from H and $(C_1-C_8)$alkyl;

$R_{8'}$ is selected from H, OR, $NR_{15'}R_{16'}$, NH—NHR$_{15'}$, SH, CN, $N_3$ and halogen; wherein R is selected from H and $(C_1-C_8)$alkyl, and $R_{15'}$ and $R_{16'}$ are independently selected from H, $(C_1-C_8)$alkyl, $(C_1-C_8)$alkyl-$(C_5-C_{12})$aryl and —CHR$_{AA}$CO$_2$H wherein R$_{AA'}$ is a side chain selected from a proteinogenic or non-proteinogenic amino acid;

Y' is selected from CH, CH$_2$, CHCH$_3$, C(CH$_3)_2$ and CCH$_3$;

n is an integer selected from 1 to 3;

- - - represents the point of attachment;

═══ represents a single or double bond according to Y'; and

∿∿∿ represents the alpha or beta anomer depending on the position of $R_1$;

$R_8$ is selected from H, OR, $NR_{15}R_{16}$, NH—$NHR_{15}$, SH, CN, $N_3$ and halogen; wherein R is selected from H and $(C_1-C_8)$alkyl, and $R_{15}$ and $R_{16}$ are independently selected from H, $(C_1-C_8)$alkyl, $(C_1-C_8)$alkyl-$(C_5-C_{12})$aryl and —$CHR_{AA}CO_2H$ wherein $R_{AA}$ is a side chain selected from a proteinogenic or non-proteinogenic amino acid;

Y is selected from CH, $CH_2$, $CHCH_3$, $C(CH_3)_2$ and $CCH_3$;

≡ represents a single or double bond according to Y; and

∿ represents the alpha or beta anomer depending on the position of $R_1$, for use in the treatment of sickle cell disease.

According to one embodiment, X represents an oxygen.

According to one embodiment, $R_1$ and $R_6$ are identical and represent hydrogen.

According to one embodiment, $R_3$ and $R_4$ are identical and represent hydrogen.

According to one embodiment, $R_2$ and R are identical and represent OH.

According to one embodiment, Y is selected from CH and $CH_2$.

According to one embodiment, wherein $R_7$ is selected from $P(O)R_9R_{10}$ or

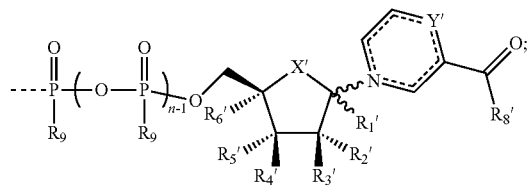

wherein $R_9$ and $R_{10}$ are as described in above and wherein:
X' is an oxygen;
$R_{1'}$ and $R_{6'}$ each represents a hydrogen;
$R_{2'}$, $R_{3'}$, $R_{4'}$ and $R_{5'}$ are independently selected from hydrogen and OH;
$R_{8'}$ is $NH_2$;
Y' is selected from CH and $CH_2$;
n is equal to 2;
- - - represents the point of attachment;
≡ represents a single or double bond depending on Y'; and
∿ represents the alpha or beta anomer depending on the position of $R_{1'}$.

According to one embodiment, $R_8$ is $NH_2$.

According to one embodiment, the compound according to the invention is selected from:

| Compounds (anomers) | Structure |
|---|---|
| 001 (beta) | 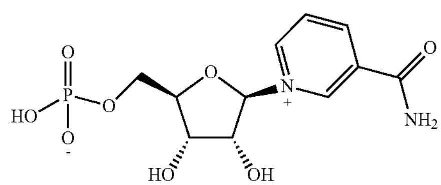 |
| 002 (alpha) | 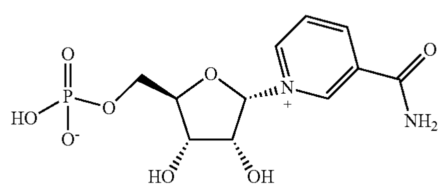 |
| 003 (beta) | 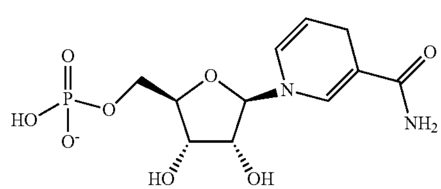 [SMILES: NC(=O)C1=CN([C@@H]2O[C@H](COP(=O)([O-])O)[C@@H](O)[C@H]2O)C=CC1] |
| 004 (alpha) | 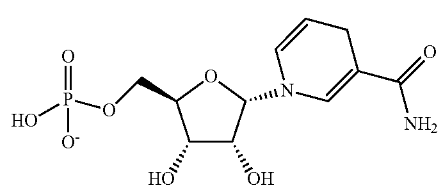 [SMILES: NC(=O)C1=CN([C@H]2O[C@H](COP(=O)([O-])O)[C@@H](O)[C@H]2O)C=CC1] |

-continued
| Compounds (anomers) | Structure |
|---|---|
| 009 (beta, beta) | 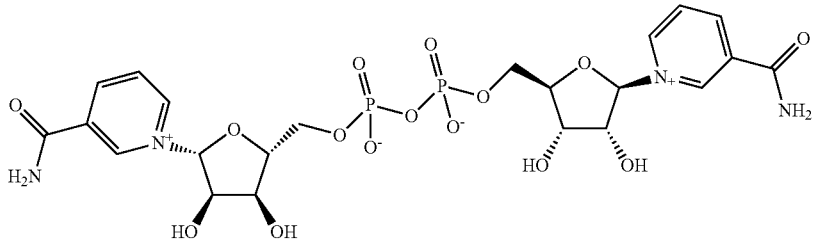 [SMILES: NC(=O)c1ccc[n+]([C@@H]2O[C@H](COP(=O)([O-])OP(=O)([O-])OC[C@H]3O[C@@H]([n+]4cccc(C(N)=O)c4)[C@H](O)[C@@H]3O)[C@@H](O)[C@H]2O)c1] |
| 010 (beta, alpha) | 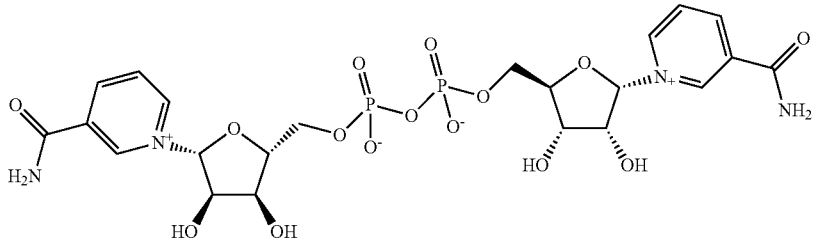 [SMILES: NC(=O)c1ccc[n+]([C@@H]2O[C@H](COP(=O)([O-])OP(=O)([O-])OC[C@H]3O[C@H]([n+]4cccc(C(N)=O)c4)[C@H](O)[C@@H]3O)[C@@H](O)[C@H]2O)c1] |
| 011 (alpha, alpha) | 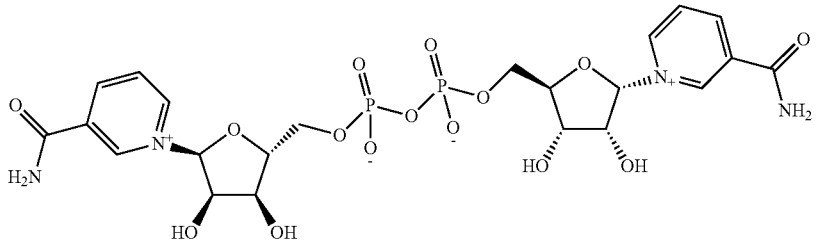 |
| 012 (beta, beta) | 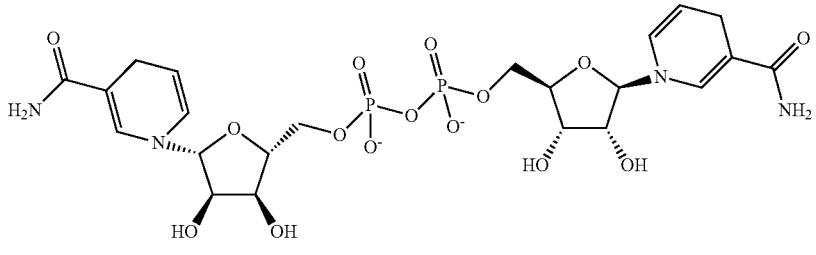 [SMILES: NC(=O)C1=CN([C@@H]2O[C@H](COP(=O)([O-])OP(=O)([O-])OC[C@H]3O[C@@H](N4C=CCC(C(N)=O)=C4)[C@H](O)[C@@H]3O)[C@@H](O)[C@H]2O)C=CC1] |
| 013 (beta, alpha) | 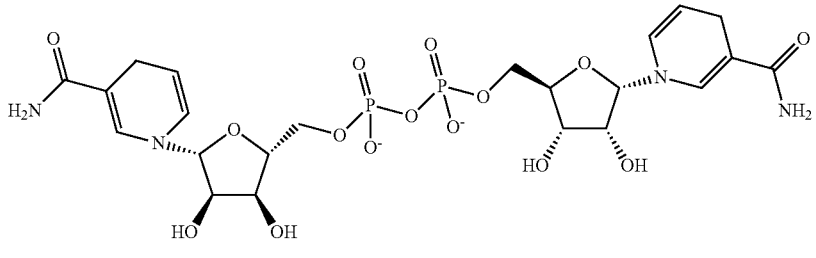 [SMILES: NC(=O)C1=CN([C@@H]2O[C@H](COP(=O)([O-])OP(=O)([O-])OC[C@H]3O[C@H](N4C=CCC(C(N)=O)=C4)[C@H](O)[C@@H]3O)[C@@H](O)[C@H]2O)C=CC1] |
| 014 (alpha, alpha) | 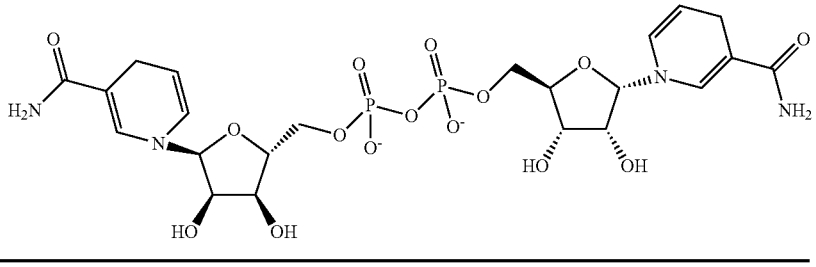 | and pharmaceutically acceptable salts and solvates thereof.

According to one embodiment, the compound according to the invention is selected from compounds 001, 002, 009, 010 and 011.

The present invention further relates to a pharmaceutical composition for use in the treatment of sickle cell disease, comprising at least one compound of formula (I) as defined herein above and at least one pharmaceutically acceptable carrier.

According to one embodiment, the pharmaceutical composition for use according to the invention, comprises in addition to the at least one compound of formula (I) as defined herein above, at least one other active ingredient selected from, but not limited to, a natural extract; opioid or non-opioid analgesics; NSAIDS; antidepressants; anticonvulsants; antibiotics; antioxidant such as CoQ10 and PQQ (Pyrroloquinoline quinone); hydroxyurea, L-glutamine, Kynurenine, kynurenic acid, tryptophan, Voxelotor and Crizanlizumab.

DEFINITIONS

The definitions and explanations below are for the terms as used throughout the entire application, including both the specification and the claims.

When describing the compounds of the invention, the terms used are to be construed in accordance with the following definitions, unless indicated otherwise.

Unless indicated otherwise, the nomenclature of substituents that are not explicitly defined herein are arrived at by naming the adjacent functionality toward the point of attachment followed by the terminal portion of the functionality. For example, the substituent "arylalkyl" refers to the group -(aryl)-(alkyl).

In the present invention, the following terms have the following meanings:

The term "alkyl" by itself or as part of another substituent refers to a hydrocarbyl radical of Formula $C_nH_{2n+1}$ wherein n is a number greater than or equal to 1. Generally, alkyl groups of this invention comprise from 1 to 12 carbon atoms, preferably from 1 to 10 carbon atoms, preferably from 1 to 8 carbon atoms, more preferably from 1 to 6 carbon atoms, still more preferably 1 to 2 carbon atoms. Alkyl groups may be linear or branched. Suitable alkyl groups include methyl, ethyl, n-propyl, i-propyl, n-butyl, i-butyl, s-butyl and t-butyl, pentyl and its isomers (e.g. n-pentyl, iso-pentyl), hexyl and its isomers (e.g. n-hexyl, isohexyl), heptyl and its isomers (e.g. n-heptyl, iso-heptyl), octyl and its isomers (e.g. n-octyl, iso-octyl), nonyl and its isomers (e.g. n-nonyl, iso-nonyl), decyl and its isomers (e.g. n-decyl, iso-decyl), undecyl and its isomers, dodecyl and its isomers. Preferred alkyl groups include methyl, ethyl, n-propyl, i-propyl, n-butyl, i-butyl, s-butyl, t-butyl, n-pentyl, n-hexyl, n-heptyl, n-octyl, n-nonyl and n-decyl. Saturated branched alkyls include, without being limited to, i-propyl, s-butyl, i-butyl, t-butyl, i-pentyl, 2-methylbutyl, 3-methylbutyl, 2-methylpentyl, 3-methylpentyl, 4-methylpentyl, 2-methylhexyl, 3-methylhexyl, 4-methylhexyl, 5-methylhexyl, 2,3-dimethylbutyl, 2,3-dimethylpentyl, 2,4-dimethylpentyl, 2,3-dimethylhexyl, 2,4-dimethylhexyl, 2,5-dimethylhexyl, 2,2-dimethylpentyl, 2,2-dimethylhexyl, 3,3-dimethylpentyl, 3,3-dimethylhexyl, 4,4-dimethylhexyl, 2-ethylpentyl, 3-ethylpentyl, 2-ethylhexyl, 3-ethylhexyl, 4-ethylhexyl, 2-methyl-2-ethylpentyl, 2-methyl-3-ethylpentyl, 2-methyl-4-ethylpentyl, 2-methyl-2-ethylhexyl, 2-methyl-3-ethylhexyl, 2-methyl-4-ethylhexyl, 2,2-diethylpentyl, 3,3-diethylhexyl, 2,2-diethylhexyl, 3,3-diethylhexyl.

Cx-Cy-alkyl refers to alkyl groups which comprise x to y carbon atoms.

When the suffix "ene" ("alkylene") is used in conjunction with an alkyl group, this is intended to mean the alkyl group as defined herein having two single bonds as points of attachment to other groups. The term "alkylene" includes methylene, ethylene, methylmethylene, propylene, ethylethylene, and 1,2-dimethylethylene.

The term "alkenyl" as used herein refers to an unsaturated hydrocarbyl group, which may be linear or branched, comprising one or more carbon-carbon double bonds. Suitable alkenyl groups comprise between 2 and 12 carbon atoms, preferably between 2 and 8 carbon atoms, still more preferably between 2 and 6 carbon atoms. Examples of alkenyl groups are ethenyl, 2-propenyl, 2-butenyl, 3-butenyl, 2-pentenyl and its isomers, 2-hexenyl and its isomers, 2,4-pentadienyl and the like.

The term "alkynyl" as used herein refers to a class of monovalent unsaturated hydrocarbyl groups, wherein the unsaturation arises from the presence of one or more carbon-carbon triple bonds. Alkynyl groups typically, and preferably, have the same number of carbon atoms as described above in relation to alkenyl groups. Non limiting examples of alkynyl groups are ethynyl, 2-propynyl, 2-butynyl, 3-butynyl, 2-pentynyl and its isomers, 2-hexynyl and its isomers—and the like.

The term "alkoxy" as used herein refers to any group —O-alkyl, wherein alkyl is as defined above. Suitable alkoxy groups include for example methoxy, ethoxy, n-propoxy, isopropoxy, n-butoxy, t-butoxy, sec-butoxy, and n-pentoxy.

The term "amino acid" as used herein refers to an alpha-aminated carboxylic acid, i.e. a molecule comprising a carboxylic acid functional group and an amine functional group in alpha position of the carboxylic acid group, for example a proteinogenic amino acid or a non-proteinogenic amino acid.

The term "aryl" as used herein refers to a polyunsaturated, aromatic hydrocarbyl group having a single ring (i.e. phenyl) or multiple aromatic rings fused together (e.g. naphthyl) or linked covalently, typically containing 5 to 12 atoms; preferably 6 to 10, wherein at least one ring is aromatic. The aromatic ring may optionally include one to two additional rings (either cycloalkyl, heterocyclyl or heteroaryl) fused thereto. Aryl is also intended to include the partially hydrogenated derivatives of the carbocyclic systems enumerated herein. Non-limiting examples of aryl comprise phenyl, biphenyl, biphenylenyl, 5- or 6-tetralinyl, naphthalen-1- or -2-yl, 4-, 5-, 6- or 7-indenyl, 1-2-, 3-, 4- or 5-acenaphthylenyl, 3-, 4- or 5-acenaphthenyl, 1- or 2-pentalenyl, 4- or 5-indanyl, 5-, 6-, 7- or 8-tetrahydronaphthyl, 1,2,3,4-tetrahydronaphthyl, 1,4-dihydronaphthyl, 1-, 2-, 3-, 4- or 5-pyrenyl.

The term "cycloalkyl" as used herein is a cyclic alkyl, alkenyl or alkynyl group, that is to say, a monovalent, saturated, or unsaturated hydrocarbyl group having 1 or 2 cyclic structures. Cycloalkyl includes monocyclic or bicyclic hydrocarbyl groups. Cycloalkyl groups may comprise 3 or more carbon atoms in the ring and generally, according to this invention comprise from 3 to 10, more preferably from 3 to 8 carbon atoms still more preferably from 3 to 6 carbon atoms. Examples of cycloalkyl groups include, but are not limited to, cyclopropyl, cyclobutyl, cyclopentyl, cyclohexyl, with cyclopropyl being particularly preferred.

The term "halo" or "halogen" means fluoro, chloro, bromo, or iodo. Preferred halo groups are fluoro and chloro.

The term "haloalkyl" alone or as part of another group, refers to an alkyl radical having the meaning as defined above wherein one or more hydrogen atoms are replaced with a halogen as defined above. Non-limiting examples of such haloalkyl radicals include chloromethyl, 1-bromoethyl, fluoromethyl, difluoromethyl, trifluoromethyl, 1,1,1-trifluoroethyl and the like. Cr-Cy-haloalkyl are alkyl groups which comprise x to y carbon atoms. Preferred haloalkyl groups are difluoromethyl and trifluoromethyl.

The term "heteroalkyl" means an alkyl group as defined above in which one or more carbon atoms are replaced by a heteroatom selected from oxygen, nitrogen and sulfur atoms. In heteroalkyl groups, the heteroatoms are linked along the alkyl chain only to carbon atoms, i.e. each heteroatom is separated from any other heteroatom by at least one carbon atom. However, the nitrogen and sulphur heteroatoms may optionally be oxidized and the nitrogen heteroatoms may optionally be quaternized. A heteroalkyl is bonded to another group or molecule only through a carbon atom, i.e. the bonding atom is not selected from the heteroatoms included in the heteroalkyl group.

Where at least one carbon atom in an aryl group is replaced with a heteroatom, the resultant ring is referred to herein as a heteroaryl ring.

The term "heteroaryl" as used herein by itself or as part of another group refers to 5 to 12 carbon-atom aromatic rings or ring systems containing 1 to 2 rings which are fused together or linked covalently, typically containing 5 to 6 atoms; at least one of which is aromatic, in which one or more carbon atoms in one or more of these rings is replaced by oxygen, nitrogen and/or sulfur atoms where the nitrogen and sulfur heteroatoms may optionally be oxidized and the nitrogen heteroatoms may optionally be quaternized. Such rings may be fused to an aryl, cycloalkyl, heteroaryl or heterocyclyl ring. Non-limiting examples of such heteroaryl, include: furanyl, thiophenyl, pyrazolyl, imidazolyl, oxazolyl, isoxazolyl, thiazolyl, isothiazolyl, triazolyl, oxadiazolyl, thiadiazolyl, tetrazolyl, oxatriazolyl, thiatriazolyl, pyridinyl, pyrimidyl, pyrazinyl, pyridazinyl, oxazinyl, dioxinyl, thiazinyl, triazinyl, imidazo[2,1-b][1,3] thiazolyl, thieno[3,2-b]furanyl, thieno[3,2-b]thiophenyl, thieno[2,3-d][1,3]thiazolyl, thieno[2,3-d]imidazolyl, tetrazolo[1,5-a]pyridinyl, indolyl, indolizinyl, isoindolyl, benzofuranyl, isobenzofuranyl, benzothiophenyl, isobenzothiophenyl, indazolyl, benzimidazolyl, 1,3-benzoxazolyl, 1,2-benzisoxazolyl, 2,1-benzisoxazolyl, 1,3-benzothiazolyl, 1,2-benzoisothiazolyl, 2,1-benzoisothiazolyl, benzotriazolyl, 1,2,3-benzoxadiazolyl, 2,1,3-benzoxadiazolyl, 1,2,3-benzothiadiazolyl, 2,1,3-benzothiadiazolyl, thienopyridinyl, purinyl, imidazo[1,2-a]pyridinyl, 6-oxo-pyridazin-l(6H)-yl, 2-oxopyridin-l(2H)-yl, 6-oxo-pyridazin-l(6H)-yl, 2-oxopyridin-l(2H)-yl, 1,3-benzodioxolyl, quinolinyl, isoquinolinyl, cinnolinyl, quinazolinyl, quinoxalinyl.

Where at least one carbon atom in a cycloalkyl group is replaced with a heteroatom, the resultant ring is referred to herein as "heterocycloalkyl" or "heterocyclyl".

The terms "heterocyclyl", "heterocycloalkyl" or "heterocyclo" as used herein by itself or as part of another group refer to non-aromatic, fully saturated or partially unsaturated cyclic groups (for example, 3 to 7 member monocyclic, 7 to 11 member bicyclic, or containing a total of 3 to 10 ring atoms) which have at least one heteroatom in at least one carbon atom-containing ring. Each ring of the heterocyclic group containing a heteroatom may have 1, 2, 3 or 4 heteroatoms selected from nitrogen, oxygen and/or sulfur atoms, where the nitrogen and sulfur heteroatoms may optionally be oxidized and the nitrogen heteroatoms may optionally be quaternized. Any of the carbon atoms of the heterocyclic group may be substituted by oxo (for example piperidone, pyrrolidinone). The heterocyclic group may be attached at any heteroatom or carbon atom of the ring or ring system, where valence allows. The rings of multi-ring heterocycles may be fused, bridged and/or joined through one or more spiro atoms. Non limiting exemplary heterocyclic groups include oxetanyl, piperidinyl, azetidinyl, 2-imidazolinyl, pyrazolidinyl imidazolidinyl, isoxazolinyl, oxazolidinyl, isoxazolidinyl, thiazolidinyl, isothiazolidinyl, piperidinyl, 3H-indolyl, indolinyl, isoindolinyl, 2-oxopiperazinyl, piperazinyl, homopiperazinyl, 2-pyrazolinyl, 3-pyrazolinyl, tetrahydro-2H-pyranyl, 2H-pyranyl, 4H-pyranyl, 3,4-dihydro-2H-pyranyl, 3-dioxolanyl, 1,4-dioxanyl, 2,5-dioximidazolidinyl, 2-oxopiperidinyl, 2-oxopyrrolodinyl, tetrahydropyranyl, tetrahydrofuranyl, tetrahydroquinolinyl, tetrahydroisoquinolin-1-yl, tetrahydroisoquinolin-2-yl, tetrahydroisoquinolin-3-yl, tetrahydroisoquinolin-4-yl, thiomorpholin-4-yl, thiomorpholin-4-ylsulfoxide, thiomorpholin-4-ylsulfone, 1,3-dioxolanyl, 1,4-oxathianyl, 1H-pyrrolizinyl, tetrahydro-1,1-dioxothiophenyl, N-formylpiperazinyl, and morpholin-4-yl.

The term "hydroxyalkyl" refers to an alkyl radical having the meaning as defined above wherein one or more hydrogen atoms are replaced with —OH moieties.

The term "thio-alkyl" refers to an alkyl radical having the meaning as defined above wherein one or more hydrogen atoms are replaced with —SH moieties.

The term "non-proteinogenic amino acid" as used herein refers to an amino acid not naturally encoded or found in the genetic code of living organism. Non limiting examples of non-proteinogenic amino acid are ornithine, citrulline, argininosuccinate, homoserine, homocysteine, cysteinesulfinic acid, 2-aminomuconic acid, δ-aminolevulinic acid, β-alanine, cystathionine, γ-aminobutyrate, DOPA, 5-hydroxytryptophan, D-serine, ibotenic acid, α-aminobutyrate, 2-aminoisobutyrate, D-leucine, D-valine, D-alanine or D-glutamate.

The term "proteinogenic amino acid" as used herein refers to an amino acid that is incorporated into proteins during translation of messenger RNA by ribosomes in living organisms, i.e. Alanine (ALA), Arginine (ARG), Asparagine (ASN), Aspartate (ASP), Cysteine (CYS), Glutamate (glutamic acid) (GLU), Glutamine (GLN), Glycine (GLY), Histidine (HIS), Isoleucine (ILE), Leucine (LEU), Lysine (LYS), Methionine (MET), Phenylalanine (PHE), Proline (PRO), Pyrrolysine (PYL), Selenocysteine (SEL), Serine (SER), Threonine (THR), Tryptophan (TRP), Tyrosine (TYR) or Valine (VAL).

The term "prodrug" as used herein means the pharmacologically acceptable derivatives of compounds of Formula (I) such as esters whose in vivo biotransformation product is the active drug. Prodrugs are characterized by increased bio-availability and are readily metabolized into the active compounds in vivo. Suitable prodrugs for the purpose of the invention include phosphoramidates, HepDirect, (S)-acyl-2-thioethyl (SATE), carboxylic esters, in particular alkyl esters, aryl esters, acyloxyalkyl esters, and dioxolene carboxylic esters; ascorbic acid esters.

The term "substituent" or "substituted" means that a hydrogen radical on a compound or group is replaced by any desired group which is substantially stable under the reaction conditions in an unprotected form or when protected by a protecting group. Examples of preferred substituents include, without being limited to, halogen (chloro, iodo, bromo, or fluoro); alkyl; alkenyl; alkynyl, as described above; hydroxy; alkoxy; nitro; thiol; thioether; imine; cyano; amido; phosphonato; phosphine; carboxyl; thiocarbonyl; sulfonyl; sulfonamide; ketone; aldehyde; ester; oxygen (—O); haloalkyl (e.g., trifluoromethyl); cycloalkyl, which may be monocyclic or fused or non-fused polycyclic (e.g., cyclopropyl, cyclobutyl, cyclopentyl, or cyclohexyl), or a heterocycloalkyl, which may be monocyclic or fused or non-fused polycyclic (e.g., pyrrolidinyl, piperidinyl, piperazinyl, morpholinyl, or thiazinyl), monocyclic or fused or non-fused polycyclic aryl or heteroaryl (e.g., phenyl, naphthyl, pyrrolyl, indolyl, furanyl, thiophenyl, imidazolyl, oxazolyl, isoxazolyl, thiazolyl, triazolyl, tetrazolyl, pyrazolyl, pyridyl, quinolinyl, isoquinolinyl, acridinyl, pyrazinyl, pyridazinyl, pyrimidinyl, benzimidazolyl, benzothiophenyl, or benzofuranyl); amino (primary, secondary, or tertiary); $CO_2CH_3$; $CONH_2$; $OCH_2CONH_2$; $NH_2$; $SO_2NH_2$; $OCHF_2$; $CF_3$; $OCF_3$; and such moieties may also be optionally substituted by a fused-ring structure or bridge, for example —$OCH_2O$—. These substituents may optionally be further substituted with a substituent selected from such groups. In certain embodiments, the term "substituent" or the adjective "substituted" refers to a substituent selected from the group consisting of an alkyl, an alkenyl, an alkynyl, an cycloalkyl, an cycloalkenyl, a heterocycloalkyl, an aryl, a heteroaryl, an arylalkyl, a heteroarylalkyl, a haloalkyl, —$C(O)NR_{17}R_{18}$, —$NR_{19}C(O)R_{20}$, a halo, —$OR_{19}$, cyano, nitro, a haloalkoxy, —$C(O)R_{19}$, —$NR_{17}R_{18}$, —$SR_{19}$, —$C(O)OR_{19}$, —$OC(O)R_{19}$, —$NR_{19}C(O)NR_{17}R_{18}$, —$OC(O)NR_{17}R_{18}$, —$NR_{19}C(O)OR_{20}$, —$S(O)_rR_{19}$, —$NR_{19}S(O)R_{r20}$, —$OS(O)R_{r20}$, $S(O)_rNR_{17}R_{18}$, —O, —S, and —N—$R_{19}$, wherein r is 1 or 2; $R_{17}$ and $R_{18}$, for each occurrence are, independently, H, an optionally substituted alkyl, an optionally substituted alkenyl, an optionally substituted alkynyl, an optionally substituted cycloalkyl, an optionally substituted cycloalkenyl, an optionally substituted heterocycloalkyl, an optionally substituted aryl, an optionally substituted heteroaryl, an optionally substituted arylalkyl, or an optionally substituted heteroarylalkyl; or $R_{17}$ and $R_{18}$ taken together with the nitrogen to which they are attached is optionally substituted heterocycloalkyl or optionally substituted heteroaryl; and $R_{19}$ and $R_{20}$ for each occurrence are, independently, H, an optionally substituted alkyl, an optionally substituted alkenyl, an optionally substituted alkynyl, an optionally substituted cycloalkyl, an optionally substituted cycloalkenyl, an optionally substituted heterocycloalkyl, an optionally substituted aryl, an optionally substituted heteroaryl, an optionally substituted arylalkyl, or an optionally substituted heteroarylalkyl. In certain embodiments, the term "substituent" or the adjective "substituted" refers to a solubilizing group.

The bonds of an asymmetric carbon can be represented here using a solid triangle ( ▬ ), a dashed triangle ( ⋯ ) or a zigzag line ( ∿ ).

The term "active ingredient" refers to a molecule or a substance whose administration to a subject slows down or stops the progression, aggravation, or deterioration of one or more symptoms of a disease, or condition; alleviates the symptoms of a disease or condition; cures a disease or condition. According to one embodiment, the therapeutic ingredient is a small molecule, either natural or synthetic. According to another embodiment the therapeutic ingredient is a biological molecule such as for example an oligonucleotide, a siRNA, a miRNA, a DNA fragment, an aptamer, an antibody and the like.

The term "administration", or a variant thereof (e.g., "administering"), means providing the active agent or active ingredient, alone or as part of a pharmaceutically acceptable composition, to the patient in whom/which the condition, symptom, or disease is to be treated.

The term "drug" refers to any substance that causes a change in physiology or psychology of a subject when administrated to the subject. In the context of the invention, "drug" encompasses both drugs for medical use ("medicinal drug" or "active ingredient") and drugs for non-medical use, e.g., recreational drugs (e.g., psychoactive drugs).

By "pharmaceutically acceptable" it is meant that the ingredients of a pharmaceutical composition are compatible with each other and not deleterious to the patient.

The terms "pharmaceutically acceptable excipient", "pharmaceutically acceptable carrier" or "pharmaceutical vehicle" refer to an inert medium or carrier used as a solvent or diluent in which the pharmaceutically active ingredient is formulated and/or administered, and which does not produce an adverse, allergic or other reaction when administered to an animal, preferably a human being. This includes all solvents, dispersion media, coatings, antibacterial and antifungal agents, isotonic agents, absorption retardants and other similar ingredients. For human administration, preparations must meet standards of sterility, general safety and purity as required by regulatory agencies such as the FDA or EMA. For the purposes of the invention, "pharmaceutically acceptable excipient" includes all pharmaceutically acceptable excipients as well as all pharmaceutically acceptable carriers, diluents, and/or adjuvants.

The term "pharmaceutically acceptable salts" includes the acid addition and base salts. Suitable acid addition salts are formed from acids which form non-toxic salts. Examples include the acetate, adipate, aspartate, benzoate, besylate, bicarbonate/carbonate, bisulphate/sulphate, borate, camsylate, citrate, cyclamate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, pyroglutamate, saccharate, stearate, succinate, tannate, tartrate, tosylate, trifluoroacetate and xinofoate salts.

Suitable base salts are formed from bases which form non-toxic salts. Examples include the aluminum, arginine, benzathine, calcium, choline, diethylamine, 2-(diethylamino)ethanol, diolamine, ethanolamine, glycine, 4-(2-hydroxyethyl)-morpholine, lysine, magnesium, meglumine, morpholine, olamine, potassium, sodium, tromethamine and zinc salts.

Hemisalts of acids and bases may also be formed, for example, hemisulphate and hemicalcium salts.

Pharmaceutically acceptable salts of compounds of Formula (I) may be prepared by one or more of these methods:
  (i) by reacting the compound of Formula (I) with the desired acid;
  (ii) by reacting the compound of Formula (I) with the desired base;
  (iii) by removing an acid- or base-labile protecting group from a suitable precursor of the compound of Formula (I) or by ring-opening a suitable cyclic precursor, e.g., a lactone or lactam, using the desired acid; and/or
  (iv) by converting one salt of the compound of Formula (I) to another by reaction with an appropriate acid or by means of a suitable ion exchange column.

All these reactions are typically carried out in solution. The salt may precipitate from solution and be collected by filtration or may be recovered by evaporation of the solvent.

The degree of ionization in the salt may vary from completely ionized to almost non-ionized.

Although generally, with respect to the salts of the compounds of the invention, pharmaceutically acceptable salts are preferred, it should be noted that the invention in its broadest sense also includes non-pharmaceutically acceptable salts, which may for example be used in the isolation and/or purification of the compounds of the invention. For example, salts formed with optically active acids or bases may be used to form diastereoisomeric salts that can facilitate the separation of optically active isomers of the compounds of Formula (I).

The term "solvate" is used herein to describe a molecular complex comprising a compound of the invention and containing stoichiometric or sub-stoichiometric amounts of one or more pharmaceutically acceptable solvent molecule, such as ethanol. The term 'hydrate' refers to a solvate when said solvent is water.

The term "human" refers to a subject of both genders and at any stage of development (i.e., neonate, infant, juvenile, adolescent, adult).

The term "subject" refers to a mammal, preferably a human. According to the present invention, a subject is a mammal, preferably a human, suffering from a red blood cell disorder and/or one or more complications associated with a red blood cell disorder, especially sickle cell disease and/or complications associated with sickle cell disease. In one embodiment, the subject is a "patient", i.e., a mammal, preferably a human, who/which is awaiting the receipt of, or is receiving medical care or was/is/will be the object of a medical procedure or is monitored for the development of a red blood cell disorder and/or one or more complications associated with a red blood cell disorder, especially sickle cell disease and/or one or more complications associated with sickle cell disease.

The term "therapeutically effective amount" (or more simply an "effective amount") as used herein means the amount of active agent or active ingredient that is aimed at, without causing significant negative or adverse side effects to the subject in need of treatment, preventing, reducing, alleviating or slowing down (lessening) one or more of the symptoms of a red blood cell disorder and/or of the complications associated with a red blood cell disorder, especially sickle cell disease and/or complications associated with sickle cell disease.

The terms "treat", "treating" or "treatment", as used herein, refer to a therapeutic treatment, to a prophylactic (or preventative) treatment, or to both a therapeutic treatment and a prophylactic (or preventive) treatment, wherein the object is to prevent, reduce, alleviate, and/or slow down (lessen) one or more of the symptoms of a red blood cell disorder and/or of the complications associated with a red blood cell disorder, especially sickle cell disease and/or complications associated with sickle cell disease, in a subject in need thereof. In one embodiment, "treating" or "treatment" refers to a therapeutic treatment. In another embodiment, "treating" or "treatment" refers to a prophylactic or preventive treatment. In yet another embodiment, "treating" or "treatment" refers to both a prophylactic (or preventive) treatment and a therapeutic treatment.

The term "complications associated with sickle cell disease" includes, but is not limited to, acute chest syndrome, acute pain crisis, chronic pain, delayed growth and puberty, avascular necrosis, eye problems such as retinopathy, gallstones, heart problems including coronary heart disease and pulmonary hypertension, infections such as meningitis, osteomyelitis, and sepsis; joint problems, kidney problems, leg ulcers, liver problems, pregnancy problems, priapism, severe anemia, stroke, renal necrosis or silent brain injury. Complications associated with sickle cell disease generally involve a worsening of the disease or the development of new signs, symptoms or pathological changes that can spread throughout the body and affect other organs and can lead to the development of new diseases resulting from an existing disease. Complications can also occur as a result of various treatments.

DETAILED DESCRIPTION

The present invention thus relates to the use of nicotinamide mononucleotide derivatives for the treatment of a red blood cell disorder. In particular, the present invention relates to nicotinamide mononucleotide derivatives for use in the treatment of sickle cell disease.

Nicotinamide Mononucleotide Derivatives

In one embodiment, the nicotinamide mononucleotide derivative used in the present invention is a compound of Formula (I)

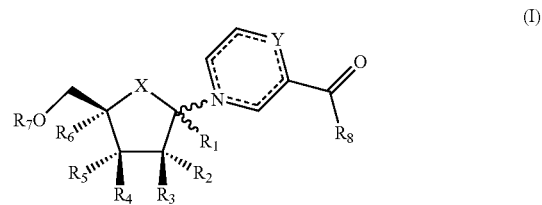

(I)

or a pharmaceutically acceptable salt or solvate thereof;
wherein:
   X is selected from O, $CH_2$, S, Se, CHF, $CF_2$ and $C=CH_2$;
   $R_1$ is selected from H, azido, cyano, $(C_1-C_8)$alkyl, $(C_1-C_8)$thio-alkyl, $(C_1-C_8)$heteroalkyl and OR; wherein R is selected from H and $(C_1-C_8)$alkyl;
   $R_2$, $R_3$, $R_4$ and $R_5$ are independently selected from H, halogen, azido, cyano, hydroxyl, $(C_1-C_{12})$alkyl, $(C_1-C_{12})$thio-alkyl, $(C_1-C_{12})$heteroalkyl, $(C_1-C_{12})$haloalkyl and OR; wherein R is selected from H, $(C_1-C_{12})$alkyl, —C(O)$(C_1-C_{12})$alkyl, —C(O)NH$(C_1-C_{12})$alkyl, —C(O)O$(C_1-C_{12})$alkyl, —C(O)aryl, —C(O)$(C_1-C_{12})$alkyl-$(C_5-C_{12})$aryl, —C(O)NH$(C_1-C_{12})$alkyl-$(C_5-C_{12})$aryl, —C(O)O$(C_1-C_{12})$alkyl-$(C_5-C_{12})$aryl and —C(O)CHR$_{AA}$NH$_2$; wherein R$_{AA}$ is a side chain selected from a proteinogenic amino acid;
   $R_6$ is selected from H, azido, cyano, $(C_1-C_8)$alkyl, $(C_1-C_8)$thio-alkyl, $(C_1-C_8)$heteroalkyl and OR; wherein R is selected from H and $(C_1-C_8)$alkyl;
   $R_7$ is selected from H, $P(O)R_9R_{10}$, $P(S)R_9R_{10}$ and

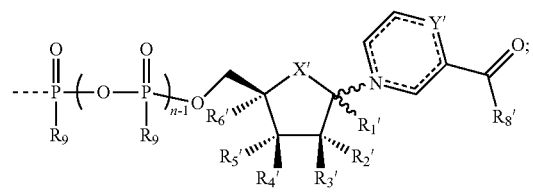

wherein:
   $R_9$ and $R_{10}$ are independently selected from OH, $OR_{11}$, $NR_{13}R_{14}$, $(C_1-C_8)$alkyl, $(C_2-C_8)$alkenyl, ($C_2$-$C_8$)alkynyl, ($C_3$-$C_{10}$)cycloalkyl, ($C_5$-$C_{12}$)aryl, ($C_5$-$C_{12}$)aryl-($C_1$-$C_8$)alkyl, ($C_1$-$C_8$)alkyl-($C_5$-$C_{12}$)aryl, ($C_1$-$C_8$)heteroalkyl, ($C_3$-$C_8$)heterocycloalkyl, ($C_5$-$C_{12}$)heteroaryl and NHC$R_\alpha R_\alpha$C(O)O$R_{12}$; wherein:

$R_{11}$ is selected from ($C_1$-$C_{10}$)alkyl, ($C_3$-$C_{10}$)cycloalkyl, ($C_5$-$C_{12}$)aryl, ($C_1$-$C_{10}$)alkyl-($C_5$-$C_{12}$)aryl, substituted ($C_5$-$C_{12}$)aryl, ($C_1$-$C_{10}$)heteroalkyl, ($C_1$-$C_{10}$)haloalkyl, —(CH$_2$)$_m$C(O)($C_1$-$C_{15}$)alkyl, —(CH$_2$)$_m$OC(O)($C_1$-$C_{15}$)alkyl, —(CH$_2$)$_m$OC(O)O($C_1$-$C_{15}$)alkyl, —(CH$_2$)$_m$SC(O)($C_1$-$C_{15}$)alkyl, —(CH$_2$)$_m$C(O)O($C_1$-$C_{15}$)alkyl, —(CH$_2$)$_m$C(O)O($C_1$-$C_{15}$)alkyl-($C_5$-$C_{12}$)aryl; wherein m is an integer selected from 1 to 8; and —P(O)(OH)OP(O)(OH)$_2$; and an internal or external counterion;

$R_{12}$ is selected from hydrogen, ($C_1$-$C_{10}$)alkyl, ($C_2$-$C_8$)alkenyl, ($C_2$-$C_8$)alkynyl, ($C_1$-$C_{10}$)haloalkyl, ($C_3$-$C_{10}$)cycloalkyl, ($C_3$-$C_{10}$)heterocycloalkyl, ($C_5$-$C_{12}$)aryl, ($C_1$-$C_4$)alkyl-($C_5$-$C_{12}$)aryl and ($C_5$-$C_{12}$)heteroaryl; wherein said aryl or heteroaryl groups are optionally substituted by one or two groups selected from halogen, trifluoromethyl, ($C_1$-$C_6$)alkyl, ($C_1$-$C_6$)alkoxy and cyano;

$R_{13}$ and $R_{14}$ are independently selected from H, ($C_1$-$C_8$)alkyl and ($C_1$-$C_8$)alkyl-($C_5$-$C_{12}$)aryl; and $R_\alpha$ and $R_{\alpha'}$ are independently selected from an hydrogen, ($C_1$-$C_{10}$)alkyl, ($C_2$-$C_{10}$)alkenyl, ($C_2$-$C_{10}$)alkynyl, ($C_3$-$C_{10}$)cycloalkyl, ($C_1$-$C_{10}$)thio-alkyl, ($C_1$-$C_{10}$)hydroxyalkyl, ($C_1$-$C_{10}$)alkyl-($C_5$-$C_{12}$)aryl, ($C_5$-$C_{12}$)aryl, —(CH$_2$)$_3$NHC(=NH)NH$_2$, (1H-indol-3-yl)methyl, (1H-imidazol-4-yl)methyl and a side chain selected from a proteinogenic or non-proteinogenic amino acid; wherein said aryl groups are optionally substituted with a group selected from hydroxyl, ($C_1$-$C_{10}$)alkyl, ($C_1$-$C_6$)alkoxy, halogen, nitro and cyano; or $R_9$ and $R_{10}$ together with the phosphorus atom to which they are attached form a 6-membered ring wherein —$R_9$–$R_{10}$— represents —O—CH$_2$—CH$_2$—CHR—O—; wherein R is selected from hydrogen, ($C_5$-$C_6$)aryl and ($C_5$-$C_6$)heteroaryl; wherein said aryl or heteroaryl groups are optionally substituted by one or two groups selected from halogen, trifluoromethyl, ($C_1$-$C_6$)alkyl, ($C_1$-$C_6$)alkoxy and cyano;

X' is selected from O, CH$_2$, S, Se, CHF, CF$_2$ and C=CH$_2$;

$R_{1'}$ is selected from H, azido, cyano, ($C_1$-$C_8$)alkyl, ($C_1$-$C_8$)thio-alkyl, ($C_1$-$C_8$)heteroalkyl and OR; wherein R is selected from H and ($C_1$-$C_8$)alkyl;

$R_{2'}$, $R_{3'}$, $R_{4'}$ and $R_{5'}$ are independently selected from H, halogen, azido, cyano, hydroxyl, ($C_1$-$C_{12}$)alkyl, ($C_1$-$C_{12}$)thio-alkyl, ($C_1$-$C_{12}$)heteroalkyl, ($C_1$-$C_{12}$)haloalkyl and OR; wherein R is selected from H, ($C_1$-$C_{12}$)alkyl, —C(O)($C_1$-$C_{12}$)alkyl, —C(O)NH($C_1$-$C_{12}$)alkyl, —C(O)O($C_1$-$C_{12}$)alkyl, —C(O)aryl, —C(O)($C_1$-$C_{12}$)alkyl-($C_5$-$C_{12}$)aryl, —C(O)NH($C_1$-$C_{12}$)alkyl-($C_5$-$C_{12}$)aryl, —C(O)O($C_1$-$C_{12}$)alkyl-$C_5$-$C_{12}$ aryl and —C(O)CHR$_{AA}$NH$_2$; wherein R$_{AA}$ is a side chain selected from a proteinogenic amino acid;

$R_{6'}$ is selected from H, azido, cyano, ($C_1$-$C_8$)alkyl, ($C_1$-$C_8$)thio-alkyl, ($C_1$-$C_8$)heteroalkyl and OR; wherein R is selected from H and ($C_1$-$C_8$)alkyl;

$R_{8'}$ is selected from H, OR, NR$_{15'}$R$_{16'}$, NH—NHR$_{15'}$, SH, CN, N$_3$ and halogen; wherein R is selected from H and ($C_1$-$C_8$)alkyl, and R$_{15'}$ and R$_{16'}$ are independently selected from H, ($C_1$-$C_8$)alkyl, ($C_1$-$C_8$)alkyl-($C_5$-$C_{12}$)aryl and —CHR$_{AA'}$CO$_2$H wherein R$_{AA'}$ is a side chain selected from a proteinogenic or non-proteinogenic amino acid;

Y' is selected from CH, CH$_2$, CHCH$_3$, C(CH$_3$)$_2$ and CCH$_3$;

n is an integer selected from 1 to 3;

- - - represents the point of attachment;

=== represents a single or double bond according to Y';  and

∿∿∿ represents the alpha or beta anomer depending on the position of $R_{1'}$, $R_8$ is selected from H, OR, NR$_{15}$R$_{16}$, NH—NHR$_{15}$, SH, CN, N$_3$ and halogen; wherein R is selected from H and ($C_1$-$C_8$)alkyl, and R$_{15}$ and R$_{16}$ are independently selected from H, ($C_1$-$C_8$)alkyl, ($C_1$-$C_8$)alkyl-($C_5$-$C_{12}$)aryl and —CHR$_{AA}$CO$_2$H wherein R$_{AA}$ is a side chain selected from a proteinogenic or non-proteinogenic amino acid;

Y is selected from CH, CH$_2$, CHCH$_3$, C(CH$_3$)$_2$ and CCH$_3$;

=== represents a single or double bond according to Y; and

∿∿∿ represents the alpha or beta anomer depending on the position of $R_1$.

In one embodiment, in Formula (I):

X is selected from O, CH$_2$, S, Se, CHF, CF$_2$ and C=CH$_2$;

$R_1$ is selected from H, azido, cyano, ($C_1$-$C_8$)alkyl, ($C_1$-$C_8$)thio-alkyl, ($C_1$-$C_8$)heteroalkyl and OR; wherein R is selected from H and ($C_1$-$C_8$)alkyl;

$R_2$, $R_3$, $R_4$ and $R_5$ are independently selected from H, halogen, azido, cyano, hydroxyl, ($C_1$-$C_{12}$)alkyl, ($C_1$-$C_{12}$)thio-alkyl, ($C_1$-$C_{12}$)heteroalkyl, ($C_1$-$C_{12}$)haloalkyl and OR; wherein R is selected from H, ($C_1$-$C_{12}$)alkyl, —C(O)($C_1$-$C_{12}$)alkyl, —C(O)NH($C_1$-$C_{12}$)alkyl, —C(O)O($C_1$-$C_{12}$)alkyl, —C(O)aryl, —C(O)($C_1$-$C_{12}$)alkyl aryl, —C(O)NH($C_1$-$C_{12}$)alkyl-($C_5$-$C_{12}$)aryl, —C(O)O($C_1$-$C_{12}$)alkyl-($C_5$-$C_{12}$)aryl and —C(O)CHR$_{AA}$NH$_2$; wherein R$_{AA}$ is a side chain selected from a proteinogenic amino acid;

$R_6$ is selected from H, azido, cyano, ($C_1$-$C_8$)alkyl, ($C_1$-$C_8$)thio-alkyl, ($C_1$-$C_8$)heteroalkyl and OR; wherein R is selected from H and ($C_1$-$C_8$)alkyl;

$R_7$ is selected from H, P(O)R$_9$R$_{10}$, P(S)R$_9$R$_{10}$ and

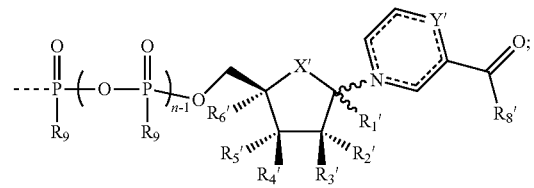

wherein:

$R_9$ and $R_{10}$ are independently selected from OH, OR$_{11}$, NHR$_{13}$, NR$_{13}$R$_{14}$, ($C_1$-$C_8$)alkyl, ($C_2$-$C_8$)alkenyl, ($C_2$-$C_8$)alkynyl, ($C_3$-$C_{10}$)cycloalkyl, ($C_5$-$C_{12}$)aryl, ($C_5$-$C_{12}$)aryl-($C_1$-$C_8$)alkyl, ($C_1$-$C_8$)alkyl-($C_5$-$C_{12}$)

aryl, $(C_1-C_8)$heteroalkyl, $(C_3-C_8)$heterocycloalkyl, $(C_5-C_{12})$heteroaryl and $NHCR_\alpha R_\alpha C(O)R_{12}$; wherein:

$R_{11}$ is selected from $(C_1-C_{10})$alkyl, $(C_3-C_{10})$cycloalkyl, $(C_5-C_{12})$aryl, $(C_1-C_{10})$alkyl-$(C_5-C_{12})$aryl, substituted $(C_5-C_{12})$aryl, $(C_1-C_{10})$heteroalkyl, $(C_1-C_{10})$haloalkyl, $—(CH_2)_mC(O)(C_1-C_{15})$alkyl, $—(CH_2)_mOC(O)(C_1-C_{15})$alkyl, $—(CH_2)_mOC(O)O(C_1-C_{15})$alkyl, $—(CH_2)_mSC(O)(C_1-C_{15})$alkyl, $—(CH_2)_mC(O)O(C_1-C_{15})$alkyl, $—(CH_2)_mC(O)O(C_1-C_{15})$alkyl aryl; wherein m is an integer selected from 1 to 8; and $—P(O)(OH)OP(O)(OH)_2$; an internal or external counterion;

$R_{12}$ is selected from hydrogen, $(C_1-C_{10})$alkyl, $(C_2-C_8)$alkenyl, $(C_2-C_8)$alkynyl, $(C_1-C_{10})$haloalkyl, $(C_3-C_{10})$cycloalkyl, $(C_3-C_{10})$cycloheteroalkyl, $(C_5-C_{12})$aryl, $(C_1-C_4)$alkyl-$(C_5-C_{12})$aryl and $(C_5-C_{12})$heteroaryl; wherein said aryl or heteroaryl groups are optionally substituted by one or two groups selected from halogen, trifluoromethyl, $(C_1-C_6)$alkyl, $(C_1-C_6)$alkoxy and cyano;

$R_{13}$ and $R_{14}$ are independently selected from H, $(C_1-C_8)$alkyl and $(C_1-C_8)$alkyl-$(C_5-C_{12})$aryl;

$R_\alpha$ and $R_{\alpha'}$ are independently selected from an hydrogen, $(C_1-C_{10})$alkyl, $(C_2-C_{10})$alkenyl, $(C_2-C_{10})$alkynyl, $(C_3-C_{10})$cycloalkyl, $(C_1-C_{10})$thio-alkyl, $(C_1-C_{10})$hydroxyalkyl, $(C_1-C_{10})$alkyl-$(C_5-C_{12})$aryl, $(C_5-C_{12})$aryl, $—(CH_2)_3NHC(=NH)NH_2$, (1H-indol-3-yl)methyl, (1H-imidazol-4-yl)methyl and a side chain selected from a proteinogenic or non-proteinogenic amino acid; wherein said aryl groups are optionally substituted with a group selected from hydroxyl, $(C_1-C_{10})$alkyl, $(C_1-C_6)$alkoxy, halogen, nitro and cyano; or $R_9$ and $R_{10}$ together with the phosphorus atoms to which they are attached form a 6-membered ring wherein $—R_9—R_{10}—$ represents $—CH_2—CH_2—CHR—$ or $—O—CH_2—CH_2—CHR—O—$; wherein R is selected from hydrogen, $(C_5-C_6)$aryl and $(C_5-C_6)$heteroaryl; wherein said aryl or heteroaryl groups are optionally substituted by one or two groups selected from halogen, trifluoromethyl, $(C_1-C_6)$alkyl, $(C_1-C_6)$alkoxy and cyano;

X' is selected from O, $CH_2$, S, Se, CHF, $CF_2$ and $C=CH_2$;

$R_{1'}$ is selected from H, azido, cyano, $(C_1-C_8)$alkyl, $(C_1-C_8)$thio-alkyl, $(C_1-C_8)$heteroalkyl and OR; wherein R is selected from H and $(C_1-C_8)$alkyl;

$R_{2'}$, $R_{3'}$, $R_{4'}$ and $R_{5'}$ are independently selected from H, halogen, azido, cyano, hydroxyl, $(C_1-C_{12})$alkyl, $(C_1-C_{12})$thio-alkyl, $(C_1-C_{12})$heteroalkyl, $(C_1-C_{12})$haloalkyl and OR; wherein R is selected from H, $(C_1-C_{12})$alkyl, $—C(O)(C_1-C_{12})$alkyl, $—C(O)NH(C_1-C_{12})$alkyl, $—C(O)O(C_1-C_{12})$alkyl, $—C(O)$aryl, $—C(O)(C_1-C_{12})$alkyl aryl, $—C(O)NH(C_1-C_{12})$alkyl-$C_5-C_{12}$ aryl, $—C(O)O(C_1-C_{12})$alkyl-$C_5-C_{12}$ aryl and $—C(O)CHR_{AA}NH_2$; wherein $R_{AA}$ is a side chain selected from a proteinogenic amino acid;

$R_{6'}$ is selected from H, azido, cyano, $(C_1-C_8)$alkyl, $(C_1-C_8)$thio-alkyl, $(C_1-C_8)$heteroalkyl and OR; wherein R is selected from H and $(C_1-C_8)$alkyl;

$R_{8'}$ is selected from H, OR, $NHR_{15'}$, $NR_{15'}R_{16'}$, NH—$NHR_{15'}$, SH, CN, $N_3$ and halogen; wherein $R_{15'}$ and $R_{16'}$ are independently selected from H, $(C_1-C_8)$alkyl and $(C_1-C_8)$alkyl-aryl;

Y' is selected from CH, $CH_2$, $C(CH_3)_2$ and $CCH_3$;

n is an integer selected from 1 to 3;

=== represents a single or double bond according to Y'; and

∿∿∿ represents the alpha or beta anomer depending on the position of $R_{1'}$;

$R_8$ is selected from H, OR, $NHR_{15}$, $NR_{15}R_{16}$, NH—$NHR_{15}$, SH, CN, $N_3$ and halogen; wherein $R_{15}$ and $R_{16}$ are independently selected from H, $(C_1-C_8)$alkyl and $(C_1-C_8)$alkyl-aryl;

Y is selected from CH, $CH_2$, $C(CH_3)_2$ and $CCH_3$;

=== represents a single or double bond according to Y; and

∿∿∿ represents the alpha or beta anomer depending on the position of $R_1$.

The nicotinamide mononucleotide derivatives of the invention may comprise one or more charged atoms. Particularly, when present, the phosphate groups may bear one or more charge, preferably one or more negative charge. Moreover, the nitrogen atom of the pyridine part of the nicotinamide group may bear one positive charge when it is quaternized. The presence of one or more charged atom in the nicotinamide mononucleotide derivatives of the invention depends on the conditions, especially pH conditions, that one skilled in the art will recognize.

According to one embodiment, X is selected from O, $CH_2$ and S. In one embodiment, X is oxygen.

According to one embodiment, $R_1$ is selected from hydrogen and OH. In one embodiment, $R_1$ is hydrogen. In one embodiment, $R_1$ is OH.

According to one embodiment, $R_2$, $R_3$, $R_4$ and $R_8$ are independently selected from hydrogen, halogen, hydroxyl, $C_1-C_{12}$ alkyl and OR; wherein R is as described herein above. In a preferred embodiment, $R_2$, $R_3$, $R_4$ and $R_8$ are independently selected from hydrogen, hydroxyl and OR; wherein R is as described herein above. In a more preferred embodiment $R_2$, $R_3$, $R_4$ and $R_8$ are independently selected from hydrogen and OH.

According to one embodiment, $R_2$ and $R_3$ are identical. In one embodiment, $R_2$ and $R_3$ are identical and represent OH. In one embodiment, $R_2$ and $R_3$ are identical and represent hydrogen.

According to one embodiment, $R_2$ and $R_3$ are different. In a preferred embodiment, $R_2$ is hydrogen and $R_3$ is OH. In a more preferred embodiment, $R_2$ is OH and $R_3$ is hydrogen.

According to one embodiment, $R_4$ and $R_8$ are identical. In one embodiment, $R_4$ and $R_5$ are identical and represent OH. In one embodiment, $R_4$ and $R_8$ are identical and represent hydrogen.

According to one embodiment, $R_4$ and $R_8$ are different. In a preferred embodiment, $R_4$ is OH and $R_8$ is hydrogen. In a more preferred embodiment, $R_4$ is hydrogen and $R_8$ is OH.

According to one embodiment, $R_3$ and $R_4$ are different. In one embodiment, $R_3$ is OH and $R_4$ is hydrogen. In one embodiment, $R_3$ is hydrogen and $R_4$ is OH.

According to one embodiment, $R_3$ and $R_4$ are identical. In a preferred embodiment, $R_3$ and $R_4$ are identical and represent OH. In a more preferred embodiment, $R_3$ and $R_4$ are identical and represent hydrogen.

According to one embodiment, $R_2$ and $R_8$ are different. In one embodiment, $R_2$ is hydrogen and $R_5$ is OH. In one embodiment, $R_2$ is OH and $R_5$ is hydrogen.

According to one embodiment, $R_2$ and $R_8$ are identical. In a preferred embodiment, $R_2$ and R are identical and represent hydrogen. In a more preferred embodiment, $R_2$ and R are identical and represent OH.

According to one embodiment, $R_6$ is selected from hydrogen and OH. In one embodiment, $R_6$ is OH. In a preferred embodiment, $R_6$ is hydrogen.

According to one embodiment, $R_1$ and $R_6$ are each independently selected from hydrogen and OH. According to one embodiment, $R_1$ and $R_6$ are both hydrogen atoms.

According to one embodiment, $R_7$ is selected from hydrogen, $P(O)R_9R_{10}$ and According to one embodiment, $R_7$ is selected from $P(O)R_9R_{10}$ and According to one embodiment, $R_7$ is hydrogen. In another embodiment, $R_7$ is not a hydrogen atom.

According to one embodiment, $R_7$ is $P(O)R_9R_{10}$; wherein $R_9$ and $R_{10}$ are as described herein above. In a preferred embodiment, $R_7$ is $P(O)(OH)_2$.

According to another embodiment, $R_7$ is wherein $R_{1'}$, $R_{2'}$, $R_{3'}$, $R_{4'}$, $R_{5'}$, $R_{6'}$, $R_{8'}$, $R_9$, $X'$, $Y'$, n, - - -, === and ∿∿∿ are as described herein above for compounds of Formula (I).

According to a preferred embodiment, $R_7$ is wherein:
$X'$ is selected from O, $CH_2$ and S, preferably $X'$ is O;
$R_{1'}$ is selected from hydrogen and OH, preferably $R_{1'}$ is hydrogen;
$R_{2'}$, $R_{3'}$, $R_{4'}$ and $R_{5'}$ are independently selected from hydrogen, halogen, hydroxyl, $(C_1-C_{12})$alkyl and OR;

wherein R is as described herein above, preferably $R_{2'}$, $R_{3'}$, $R_{4'}$, and $R_{5'}$ are independently selected from hydrogen, hydroxyl and OR; wherein R is as described herein above, more preferably $R_{2'}$, $R_{3'}$, $R_{4'}$, and $R_{5'}$ are independently selected from hydrogen and OH;
$R_{6'}$ is selected from hydrogen or OH, preferably $R_{6'}$ is hydrogen;
$R_{8'}$ is selected from H, OR, and $NR_{15'}R_{16'}$; wherein $R_{15'}$ and $R_{16'}$ are as described herein above, preferably $R_{8'}$ is $NHR_{15'}$; wherein $R_{15'}$ is as described herein above, more preferably $R_{8'}$ is $NH_2$;
$Y'$ is selected from CH and $CH_2$
n is an integer selected from 1 to 3;
- - - represents the point of attachment;
=== represents a single or double bond depending on $Y'$; and
∿∿∿ represents the alpha or beta anomer depending on the position of $R_{1'}$.

According to one embodiment, in Formula (I), $R_7$ is

X and $X'$ are independently selected from O, $CH_2$ and S, preferably X and $X'$ are O;
$R_1$ and $R_{1'}$ are independently selected from hydrogen and OH, preferably $R_1$ and $R_{1'}$ are hydrogen;
$R_2$, $R_3$, $R_4$, $R_5$, $R_{2'}$, $R_{3'}$, $R_{4'}$ and $R_{5'}$ are independently selected from hydrogen, halogen, hydroxyl, $(C_1-C_{12})$ alkyl and OR; wherein R is as described herein above, preferably $R_2$, $R_3$, $R_4$, $R_5$, $R_{2'}$, $R_{3'}$, $R_{4'}$ and $R_{5'}$ are independently selected from hydrogen, hydroxyl and OR; wherein R is as described herein above, more preferably $R_2$, $R_3$, $R_4$, $R_5$, $R_{2'}$, $R_{3'}$, $R_{4'}$ and $R_{5'}$ are independently selected from hydrogen and OH;
$R_6$ and $R_{6'}$ are independently selected from hydrogen and OH, preferably $R_6$ and $R_{6'}$ are hydrogen;
$R_8$ and $R_{8'}$ are independently selected from H, OR and $NR_{15'}R_{16'}$; wherein $R_{15'}$ and $R_{16'}$ are as described herein above, preferably $R_8$ and $R_{8'}$ are $NHR_{15'}$; wherein $R_{15'}$ is as described herein above, more preferably $R_8$ and $R_{8'}$ are $NH_2$;
Y and $Y'$ are independently selected from CH and $CH_2$;
n is an integer selected from 1 to 3;
- - - represents the point of attachment;
=== represents a single or double bond depending on Y and $Y'$; and
∿∿∿ represents the alpha or beta anomers depending on the position of $R_1$ and $R_{1'}$.

According to one embodiment, n is 1. According to one embodiment, n is 2. According to one embodiment, n is 3.

According to one embodiment, $R_8$ is selected from H, OR, and $NR_{15}R_{16}$; wherein $R_{15}$ and $R_{16}$ are as described herein above. In a preferred embodiment, $R_8$ is $NHR_{15}$; wherein $R_{15}$ is as described herein above. In one embodiment, $R_8$ is $NH_2$.

According to one embodiment, Y is a CH or $CH_2$. In one embodiment, Y is a CH. In one embodiment, Y is a $CH_2$.

According to some embodiments, the nicotinamide mononucleotide derivative used in the present invention is of general Formula (II):

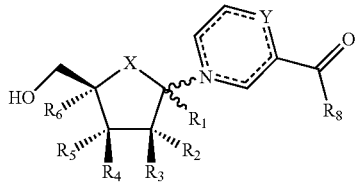

(II)

or a pharmaceutically acceptable salt or solvate thereof; wherein $R_1$, $R_2$, $R_3$, $R_4$, $R_5$, $R_6$, $R_8$, X, Y, $\mathrel{\vcenter{\hbox{\rule{1em}{0.4pt}}}}$ and ⁓ are as described herein above for compounds of Formula (I).

According to some embodiments, preferred compounds of general Formula (II) are those of Formula (II-1):

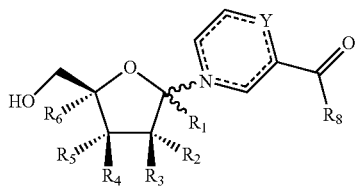

(II-1)

or a pharmaceutically acceptable salt or solvate thereof; wherein $R_1$, $R_2$, $R_3$, $R_4$, $R_5$, $R_6$, $R_8$, Y, $\mathrel{\vcenter{\hbox{\rule{1em}{0.4pt}}}}$ and ⁓ are as described herein above for compounds of Formula (I).

According to some embodiments, preferred compounds of general Formula (II) are those of Formula (II-2):

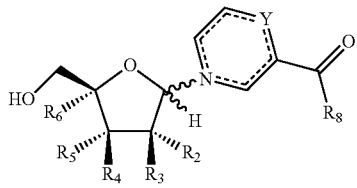

(II-2)

or a pharmaceutically acceptable salt or solvate thereof; wherein $R_2$, $R_3$, $R_4$, $R_5$, $R_6$, $R_8$, Y, $\mathrel{\vcenter{\hbox{\rule{1em}{0.4pt}}}}$ and ⁓ are as described herein above for compounds of Formula (I).

According to some embodiments, preferred compounds of general Formula (II) are those of Formula (II-3):

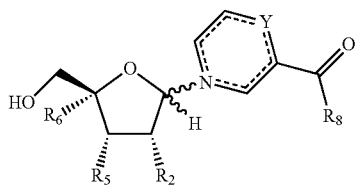

(II-3)

or a pharmaceutically acceptable salt or solvate thereof; wherein $R_2$, $R_5$, $R_6$, $R_8$, Y, $\mathrel{\vcenter{\hbox{\rule{1em}{0.4pt}}}}$ and ⁓ are as described herein above for compounds of Formula (I).

According to some embodiments, preferred compounds of general Formula (II) are those of Formula (II-4):

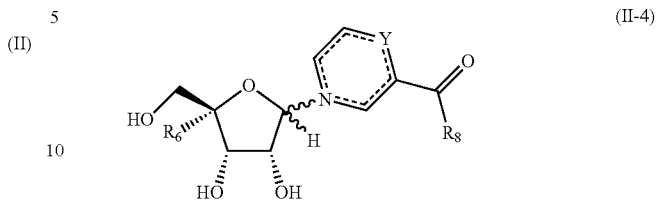

(II-4)

or a pharmaceutically acceptable salt or solvate thereof; wherein $R_6$, $R_8$, Y, $\mathrel{\vcenter{\hbox{\rule{1em}{0.4pt}}}}$ and ⁓ are as described herein above for compounds of Formula (I).

According to some embodiments, preferred compounds of general Formula (II) are those of Formula (II-5):

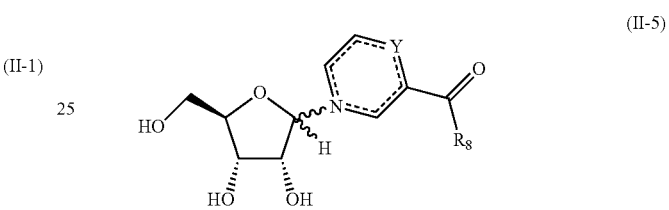

(II-5)

or a pharmaceutically acceptable salt or solvate thereof; wherein $R_8$, Y, $\mathrel{\vcenter{\hbox{\rule{1em}{0.4pt}}}}$ and ⁓ are as described herein above for compounds of Formula (I).

According to some embodiments, preferred compounds of general Formula (II) are those of Formula (II-6):

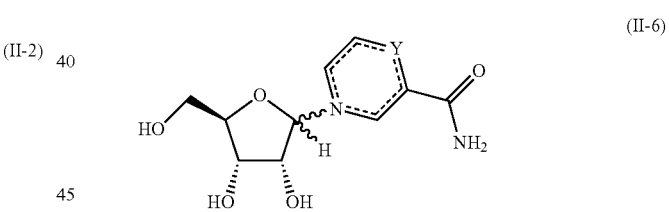

(II-6)

or a pharmaceutically acceptable salt or solvate thereof, wherein Y, $\mathrel{\vcenter{\hbox{\rule{1em}{0.4pt}}}}$ and ⁓ are as described herein above for compounds of Formula (I).

According to some embodiments, preferred compounds of general Formula (II) are those of Formula (II-7):

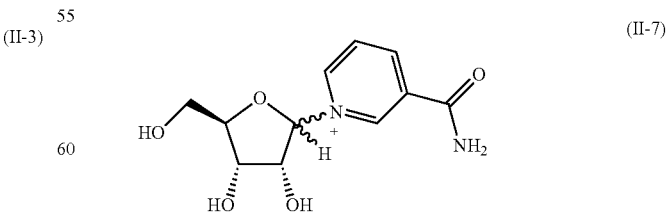

(II-7)

or a pharmaceutically acceptable salt or solvate thereof, wherein ⁓ is as described herein above for compounds of Formula (I).

According to some embodiments, the invention relates to compounds of general Formula (II-8):

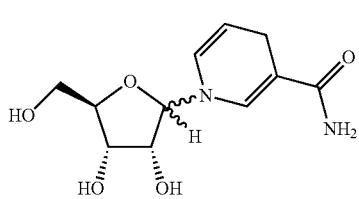

(II-8)

or a pharmaceutically acceptable salt or solvate thereof, wherein ⁓ is as described herein above for compounds of Formula (I).

According to a preferred embodiment, the nicotinamide mononucleotide derivative used in the present invention is of general Formula (III):

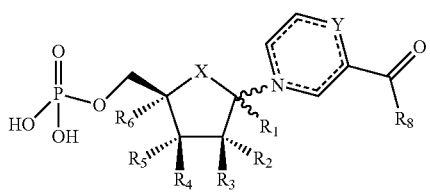

(III)

or a pharmaceutically acceptable salt or solvate thereof; wherein $R_1$, $R_2$, $R_3$, $R_4$, $R_5$, $R_6$, $R_8$, X, Y, ═══ and ⁓ are as described herein above for compounds of Formula (I).

According to one embodiment, preferred compounds of general Formula (III) are those of Formula (III-1):

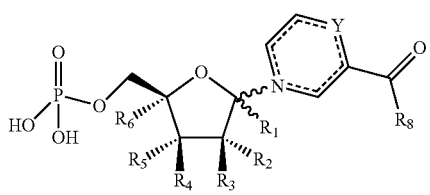

(III-1)

or a pharmaceutically acceptable salt or solvate thereof; wherein $R_1$, $R_2$, $R_3$, $R_4$, $R_5$, $R_6$, $R_8$, Y, ═══ and ⁓ are as described herein above for compounds of Formula (I).

According to one embodiment, preferred compounds of general Formula (III) are those of Formula (III-2):

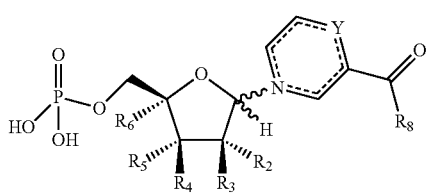

(III-2)

or a pharmaceutically acceptable salt or solvate thereof; wherein $R_2$, $R_3$, $R_4$, $R_5$, $R_6$, $R_8$, Y, ═══ and ⁓ are as described herein above for compounds of Formula (I).

According to one embodiment, preferred compounds of general Formula (III) are those of Formula (III-3):

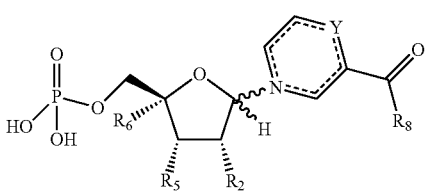

(III-3)

or a pharmaceutically acceptable salt or solvate thereof; wherein $R_2$, $R_5$, $R_6$, $R_8$, Y, ═══ and ⁓ are as described herein above for compounds of Formula (I).

According to one embodiment, preferred compounds of general Formula (III) are those of Formula (III-4):

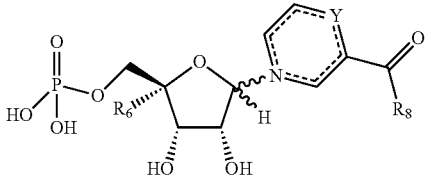

(III-4)

or a pharmaceutically acceptable salt or solvate thereof; wherein $R_6$, $R_8$, Y, ═══ and ⁓ are as described herein above for compounds of Formula (I).

According to one embodiment, preferred compounds of general Formula (III) are those of Formula (III-5):

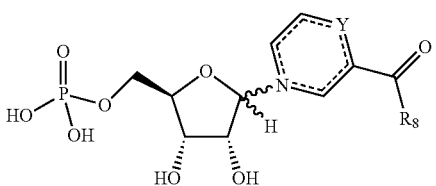

(III-5)

or a pharmaceutically acceptable salt or solvate thereof; wherein $R_8$, Y, ═══ and ⁓ are as described herein above for compounds of Formula (I).

According to one embodiment, preferred compounds of general Formula (III) are those of Formula (III-6):

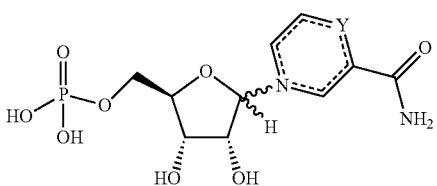

(III-6)

or a pharmaceutically acceptable salt or solvate thereof, wherein Y, ═══ and ⁓ are as described herein above for compounds of Formula (I).

According to one embodiment, preferred compounds of general Formula (III) are those of Formula (III-7):

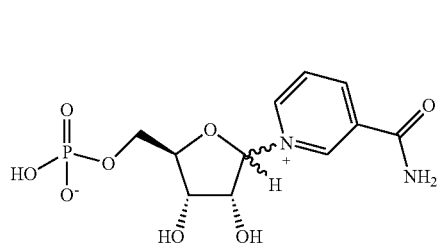
(III-7)

or a pharmaceutically acceptable salt or solvate thereof, wherein ∼∼∼ is as described herein above for compounds of Formula (I).

According to one embodiment, preferred compounds of general Formula (III) are those of Formula (III-8):

(III-8)

or a pharmaceutically acceptable salt or solvate thereof, wherein ∼∼∼ is as described herein above for compounds of Formula (I).

According to another preferred embodiment, the nicotinamide mononucleotide derivative used in the present invention is of general Formula (IV):

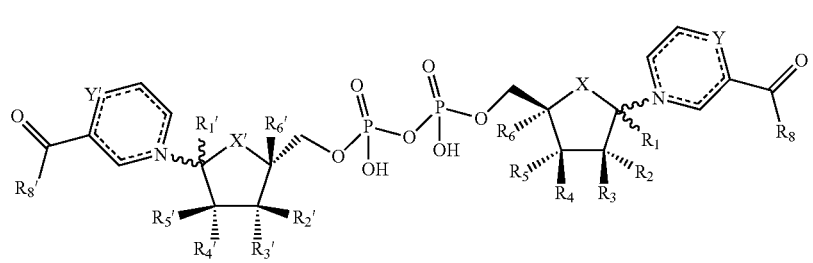
(IV)

or a pharmaceutically acceptable salt or solvate thereof, wherein $R_1$, $R_1'$, $R_2$, $R_2'$, $R_3$, $R_3'$, $R_4$, $R_4'$, $R_5$, $R_5'$, $R_6$, $R_6'$, $R_8$, $R_8'$, X, X', Y, Y', $==$ and ∼∼∼ are as described herein above for compounds of Formula (I).

According to one embodiment, preferred compounds of general Formula (IV) are those of Formula (IV-1):

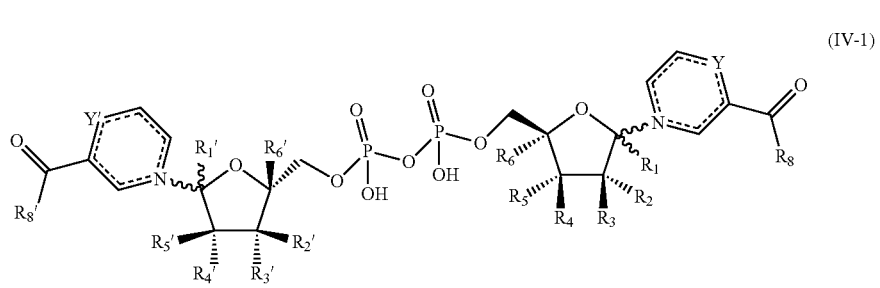
(IV-1)

or a pharmaceutically acceptable salt or solvate thereof, where wherein $R_1$, $R_1'$, $R_2$, $R_2'$, $R_3$, $R_3'$, $R_4$, $R_4'$, $R_5$, $R_5'$, $R_6$, $R_6'$, $R_8$, $R_8'$, Y, Y', $==$ and ∼∼∼ are as described herein above for compounds of Formula (I).

According to one embodiment, preferred compounds of general Formula (IV) are those of Formula (IV-2):

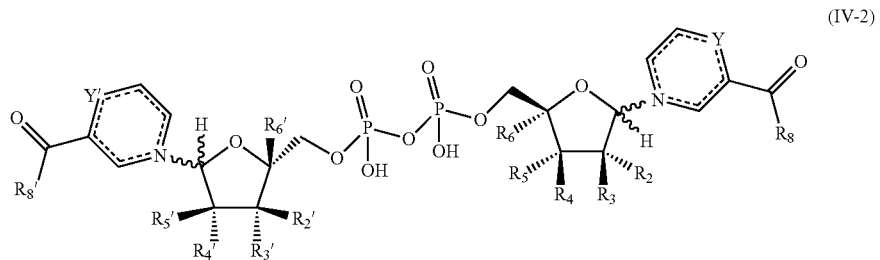
(IV-2)

or a pharmaceutically acceptable salt or solvate thereof, wherein $R_2$, $R_{2'}$, $R_3$, $R_{3'}$, $R_4$, $R_{4'}$, $R_5$, $R_{5'}$, $R_6$, $R_{6'}$, $R_8$, $R_{8'}$, Y, Y', ═══ and ∼∼∼ are as described herein above for compounds of Formula (I).

According to one embodiment, preferred compounds of general Formula (IV) are those of Formula (IV-3):

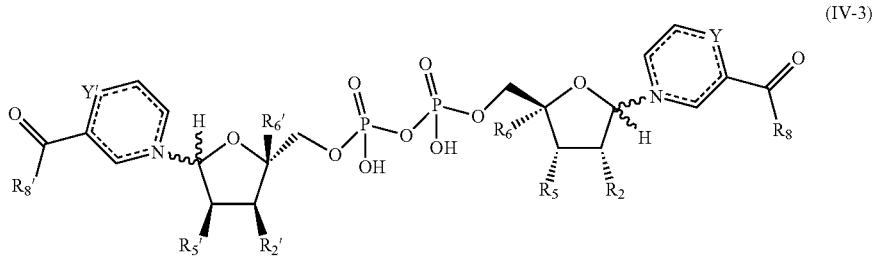

(IV-3)

or a pharmaceutically acceptable salt or solvate thereof, wherein $R_2$, $R_{2'}$, $R_5$, $R_{5'}$, $R_6$, $R_{6'}$, $R_8$, $R_{8'}$, Y, Y', ═══ and ∼∼∼ are as described herein above for compounds of Formula (I).

According to one embodiment, preferred compounds of general Formula (IV) are those of Formula (IV-4):

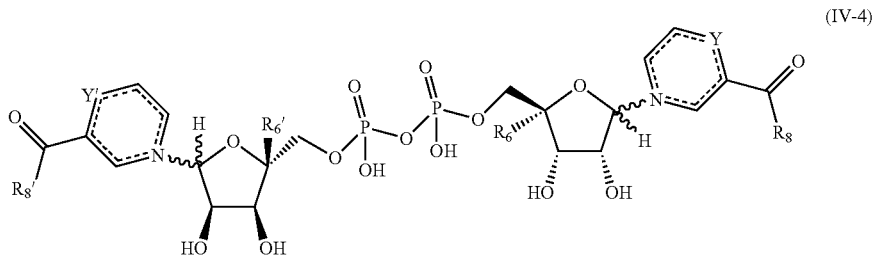

(IV-4)

or a pharmaceutically acceptable salt or solvate thereof, wherein $R_6$, $R_{6'}$, $R_8$, $R_{8'}$, Y, Y', ═══ and ∼∼∼ are as described herein above for compounds of Formula (I).

According to one embodiment, preferred compounds of general Formula (IV) are those of Formula (IV-5):

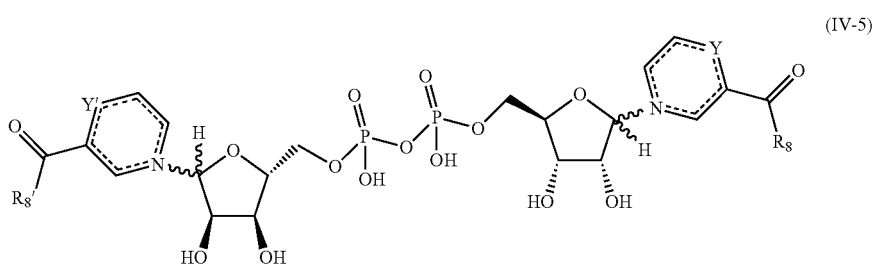

(IV-5)

or a pharmaceutically acceptable salt or solvate thereof, wherein $R_8$, $R_{8'}$, Y, Y', ═══ and ∼∼∼ are as described herein above for compounds of Formula (I).

According to one embodiment, preferred compounds of general Formula (IV) are those of Formula (IV-6):

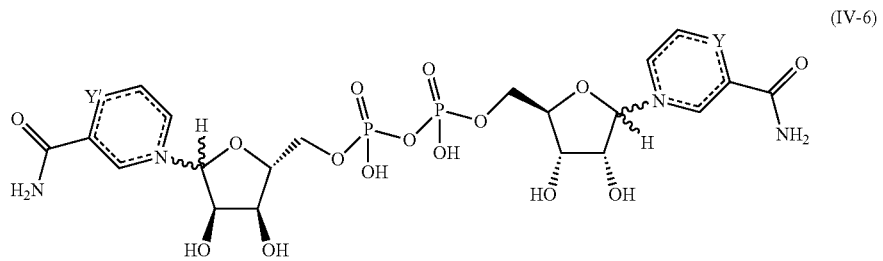

(IV-6)

or a pharmaceutically acceptable salt or solvate thereof; wherein Y, Y', ≡ and ∿∿ are as described herein above for compounds of Formula (I).

According to one embodiment, preferred compounds of general Formula (IV) are those of Formula (IV-7):

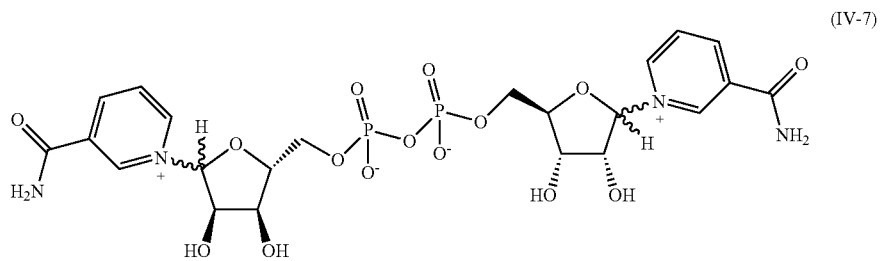

(IV-7)

or a pharmaceutically acceptable salt or solvate thereof, wherein ∿∿ is as described herein above for compounds of Formula (I).

According to one embodiment, preferred compounds of general Formula (IV) are those of Formula (IV-8):

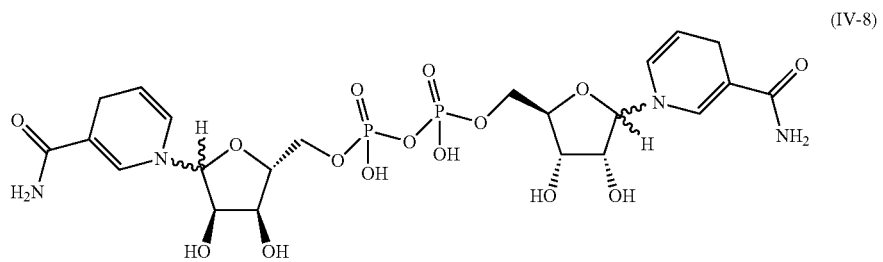

(IV-8)

or a pharmaceutically acceptable salt or solvate thereof, wherein ∿∿ is as described herein above for compounds of Formula (I).

According to one embodiment, the nicotinamide mononucleotide derivative used in the present invention is selected from compounds 001 to 014 from Table 1 below or a pharmaceutically acceptable salt or solvate thereof:

TABLE 1

| Compounds (anomers) | Structure |
|---|---|
| 001 (beta) | 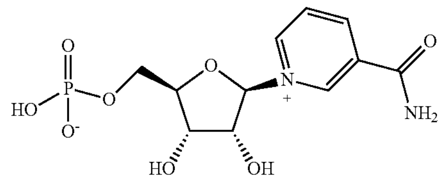 |
| 002 (alpha) | 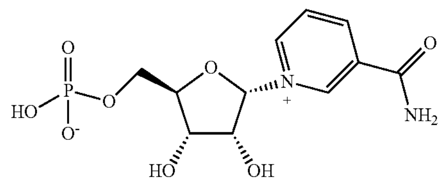 |
| 003 (beta) | 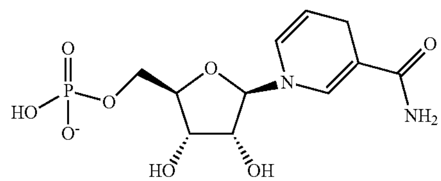 [SMILES: NC(=O)C1=CN([C@@H]2O[C@H](COP(=O)([O-])O)[C@@H](O)[C@H]2O)C=CC1] |
| 004 (alpha) | 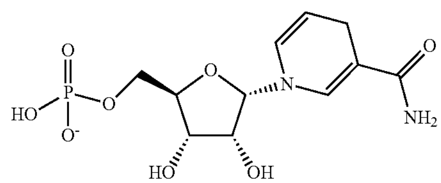 [SMILES: NC(=O)C1=CN([C@H]2O[C@H](COP(=O)([O-])O)[C@@H](O)[C@H]2O)C=CC1] |
| 005 (beta) | 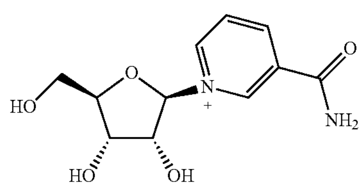 |
| 006 (alpha) | 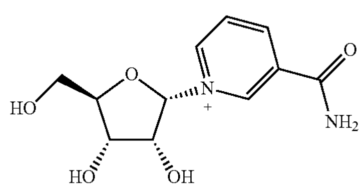 |
| 007 (beta) | 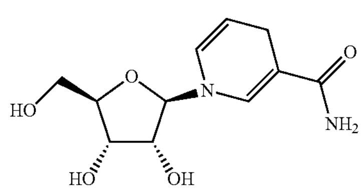 [SMILES: NC(=O)C1=CN([C@@H]2O[C@H](CO)[C@@H](O)[C@H]2O)C=CC1] |
| 008 (alpha) | 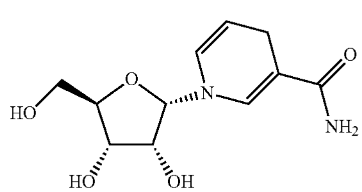 [SMILES: NC(=O)C1=CN([C@H]2O[C@H](CO)[C@@H](O)[C@H]2O)C=CC1] |

TABLE 1-continued

| Compounds (anomers) | Structure |
|---|---|
| 009 (beta, beta) | 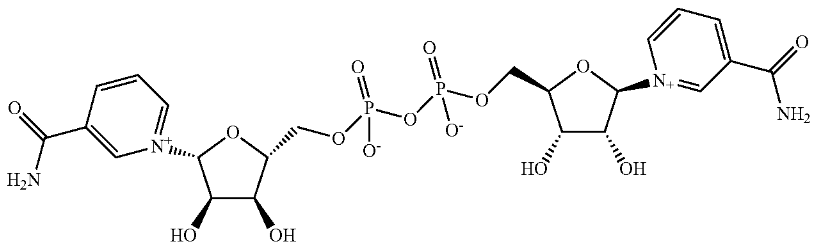 [SMILES: NC(=O)c1ccc[n+]([C@@H]2O[C@H](COP(=O)([O-])OP(=O)([O-])OC[C@H]3O[C@@H]([n+]4cccc(C(N)=O)c4)[C@H](O)[C@@H]3O)[C@@H](O)[C@H]2O)c1] |
| 010 (beta, alpha) | 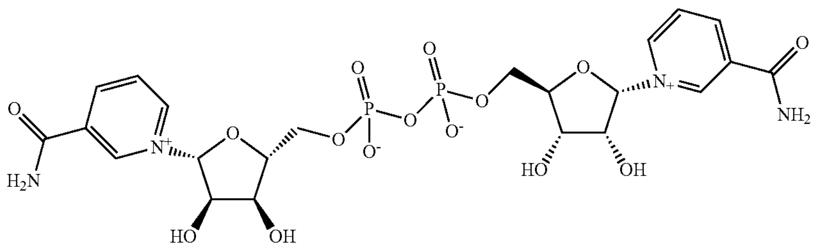 [SMILES: NC(=O)c1ccc[n+]([C@@H]2O[C@H](COP(=O)([O-])OP(=O)([O-])OC[C@H]3O[C@H]([n+]4cccc(C(N)=O)c4)[C@H](O)[C@@H]3O)[C@@H](O)[C@H]2O)c1] |
| 011 (alpha, alpha) | 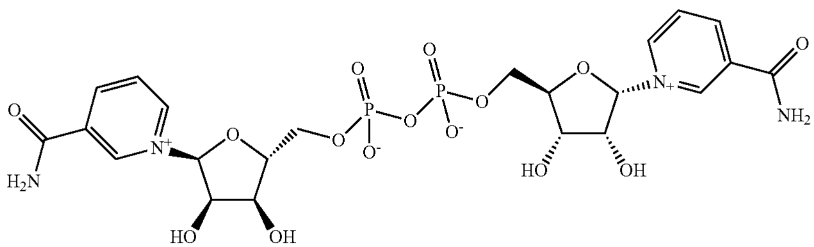 |
| 012 (beta, beta) | 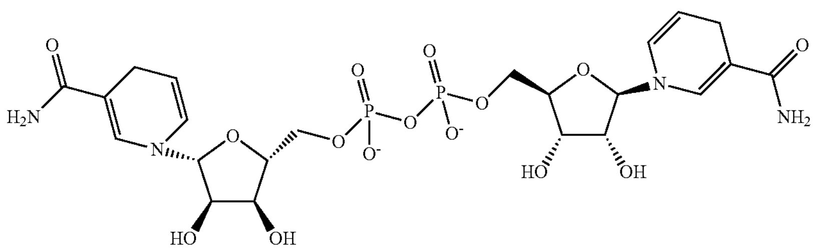 [SMILES: NC(=O)C1=CN([C@@H]2O[C@H](COP(=O)([O-])OP(=O)([O-])OC[C@H]3O[C@@H](N4C=CCC(C(N)=O)=C4)[C@H](O)[C@@H]3O)[C@@H](O)[C@H]2O)C=CC1] |
| 013 (beta, alpha) | 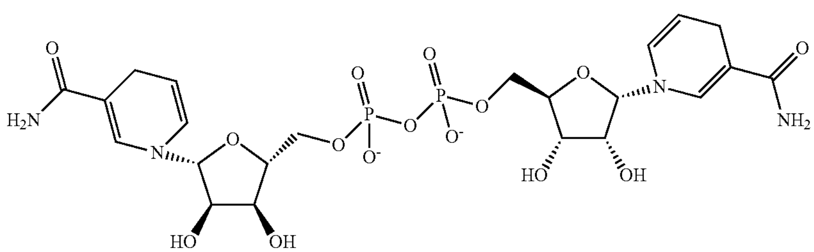 [SMILES: NC(=O)C1=CN([C@@H]2O[C@H](COP(=O)([O-])OP(=O)([O-])OC[C@H]3O[C@H](N4C=CCC(C(N)=O)=C4)[C@H](O)[C@@H]3O)[C@@H](O)[C@H]2O)C=CC1] |
| 014 (alpha, alpha) | 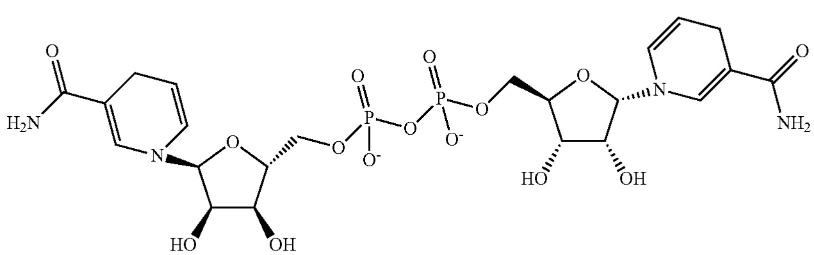 [SMILES: NC(=O)C1=CN([C@H]2O[C@H](COP(=O)([O-])OP(=O)([O-])OC[C@H]3O[C@H](N4C=CCC(C(N)=O)=C4)[C@H](O)[C@@H]3O)[C@@H](O)[C@H]2O)C=CC1] |

According to one embodiment, preferred nicotinamide mononucleotide derivatives are compounds 001 to 014 or a pharmaceutically acceptable salt or solvate thereof.

According to one embodiment, preferred nicotinamide mononucleotide derivatives are compounds 001, 002, 003, 004, 009, 010, 011, 012, 013 and 014 or a pharmaceutically acceptable salt or solvate thereof.

According to one embodiment, more preferred nicotinamide mononucleotide derivatives are compounds 001, 002, 009, 010 and 011 or a pharmaceutically acceptable salt or solvate thereof.

According to one embodiment, more preferred nicotinamide mononucleotide derivatives are compounds 001 and 002 or a pharmaceutically acceptable salt or solvate thereof.

According to another embodiment, more preferred nicotinamide mononucleotide derivatives are compounds 009, 010 and 011 or a pharmaceutically acceptable salt or solvate thereof.

According to one embodiment, even more preferred nicotinamide mononucleotide derivatives are compounds 002, 010 and 011 or a pharmaceutically acceptable salt or solvate thereof.

All references to compounds of Formula (I) and subformulae thereof include references to salts, solvates, multicomponent complexes and liquid crystals thereof. All references to compounds of Formula (I) and subformulae thereof include references to polymorphs and crystal habits thereof.

All references to compounds of Formula (I) and subformulae thereof include references to pharmaceutically acceptable prodrugs thereof.

The nicotinamide mononucleotide derivatives used in the present invention can be under the form of a pharmaceutical composition. In one embodiment, the pharmaceutical composition comprises a nicotinamide mononucleotide derivative as defined hereinabove, and at least one pharmaceutically acceptable carrier.

According to one embodiment, the pharmaceutical composition comprises, in addition to a nicotinamide mononucleotide derivative as defined hereinabove, at least one additional active ingredient, e.g., an active ingredient selected from, but not limited to, a natural extract; opioid or non-opioid analgesics; NSAIDS; antidepressants; anticonvulsants; antibiotics; antioxidant such as CoQ10 and PQQ (Pyrroloquinoline quinone); hydroxyurea, L-glutamine, Kynurenine, kynurenic acid, tryptophan, Voxelotor and Crizanlizumab.

Non limiting examples of a natural extract are glycoproteins extract; terpenoids extract containing pentacyclic triterpenes such as betulin, pentacyclic triterpene metabolite such as betulinic acid, tramspiroins, rosenolactones, sesquiterpenes, erinacins; a flavonoid extract containing flavones, flavonols, flavanones, flavanols bioflavonoids or isolfavonoids; a polysaccharide extract containing PSP, PSK, CVG, HPB-3, H6PC20; or a polyaromatic molecule such as Hericerins and hericenones; from species such as *Trametes versicolor, Hericium erinaceus, Grifola frondasa*, milk thistle, artichoke, turmeric, dandelion, yellow dock, beetroot and ginger.

Process

According to another aspect, the invention relates to a method for the preparation of the compound of Formula (I) as described hereinabove.

In particular, the compounds of Formula (I) may be prepared as described below from substrates A-E. It shall be understood by a person skilled in the art that these schemes are in no way limiting and that variations may be made without departing from the spirit and scope of this invention.

According to one embodiment, the method involves in a first step the mono-phosphorylation of a compound of Formula (A), in the presence of phosphoryl chloride and a trialkyl phosphate, to yield the phosphorodichloridate of Formula (B):

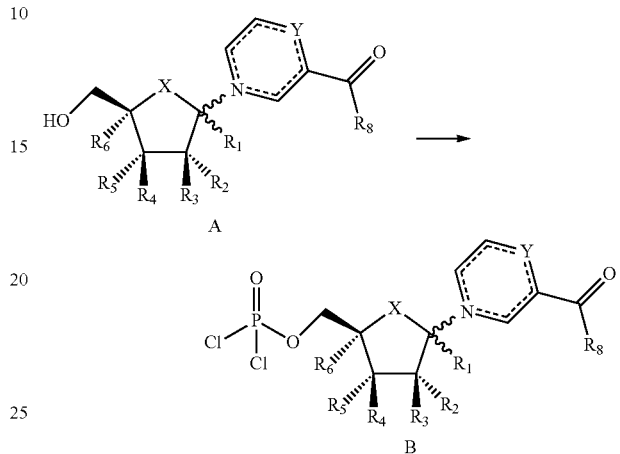

wherein X, $R_1$, $R_2$, $R_3$, $R_4$, $R_5$, $R_6$, $R_8$, Y, $=\!=\!=$ and $\sim\!\sim\!\sim$ are as described herein above.

In a second step, the phosphorodichloridate of Formula (B) is hydrolyzed to yield the phosphate of Formula (C):

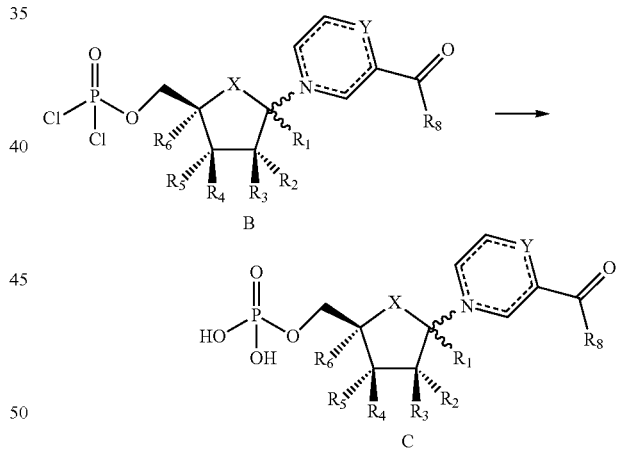

wherein X, $R_1$, $R_2$, $R_3$, $R_4$, $R_5$, $R_6$, $R_7$, $R_8$, Y, $=\!=\!=$ and $\sim\!\sim\!\sim$ are as described herein above.

In an alternative embodiment, when in Formula (I) $R_7$ is

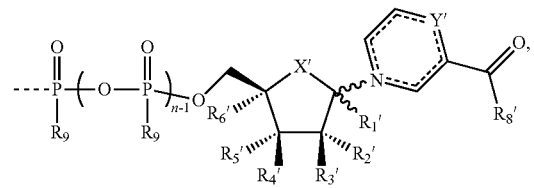

the phosphate compound of Formula (C) obtained in the second step is then reacted, with a phosphorodichloridate compound of Formula (B') obtained as described in the first step:

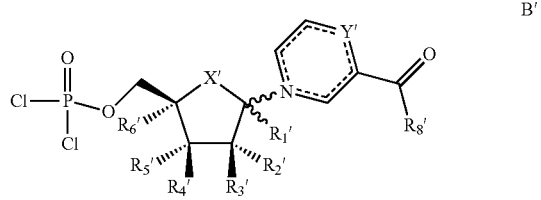

wherein $R_{1'}$, $R_{2'}$, $R_{3'}$, $R_{4'}$, $R_{5'}$, $R_{6'}$, $R_{8'}$, X', Y', === and ∿∿∿ are as described herein above; to give the compound of Formula (I) as described herein above;
followed by hydrolysis to yield the compound of Formula (I).

According to one embodiment, the compound of Formula (A) is synthesized using various methods known to the person skilled in the art.

According to one embodiment, the compound of Formula (A) wherein Y is CH, referred to as compound of Formula (A-a), is synthesized by reacting the pentose of Formula (D) with a nitrogen derivative of Formula (E) leading to the compound of Formula (A-1), which is then selectively deprotected to give the compound of Formula (A-a),

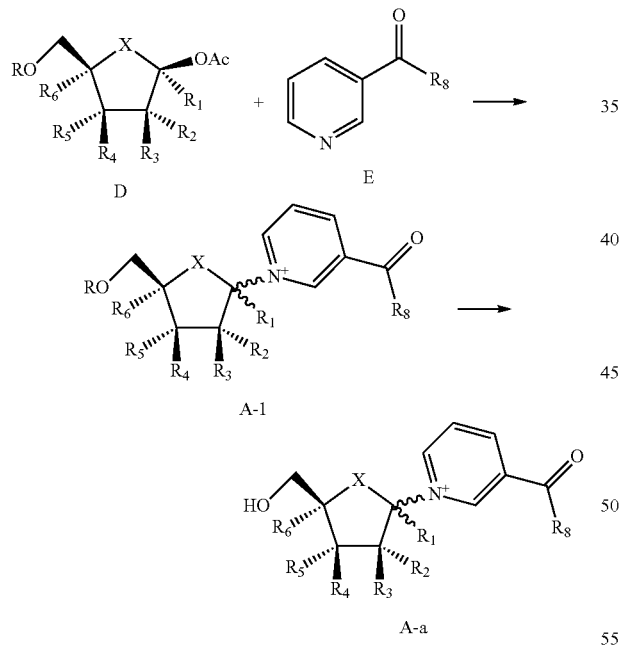

wherein X, $R_1$, $R_2$, $R_3$, $R_4$, $R_5$, $R_6$, $R_8$, Y and ∿∿∿ are as described herein above and R is a protective group.

According to one embodiment, R is an appropriate protective group known to the skilled person in the art. In one embodiment, the protecting group is selected from triarylmethyls and silyls. Non-limiting examples of triarylmethyl include trityl, monomethoxytrityl, 4,4'-dimethoxytrityl and 4,4',4"-trimethoxytrityl. Non-limiting examples of silyl groups include trimethylsilyl, tert-butyldimethylsilyl, triisopropylsilyl, tert-butyldiphenylsilyl, tri-iso-propylsilyloxymethyl and [2-(trimethylsilyl)ethoxy]methyl.

According to one embodiment, any hydroxyl group attached to the pentose is protected by an appropriate protective group known to the person skilled in the art.

The choice and exchange of protective groups is the responsibility of the person skilled in the art. Protective groups can also be removed by methods well known to the skilled person, for example, with an acid (e.g. mineral or organic acid), base or fluoride source.

According to a preferred embodiment, the nitrogen nicotinamide of Formula (E) is coupled to the pentose of Formula (D) by a reaction in the presence of a Lewis acid leading to the compound of Formula (A-1). Non-limiting examples of Lewis acids include TMSOTf, $BF_3 \cdot OEt_2$, $TiCl_4$ and $FeCl_3$.

According to one embodiment, the method of the present invention further comprises a step of reducing the compound of Formula (A-a) by various methods well known to the skilled person in the art, leading to the compound of Formula (A-b) wherein Y is $CH_2$ and X, $R_1$, $R_2$, $R_3$, $R_4$, $R_5$, $R_6$, $R_8$, === and ∿∿∿ are as defined above.

According to a specific embodiment, the present invention relates to a method for the preparation of the compounds 001, 003, 005, 007 and 009.

In a first step, the nicotinamide of Formula (E-i) is coupled to the ribose tetraacetate of Formula (D-i) by a coupling reaction in the presence of a Lewis acid, resulting in the compound of Formula (A-1-i):

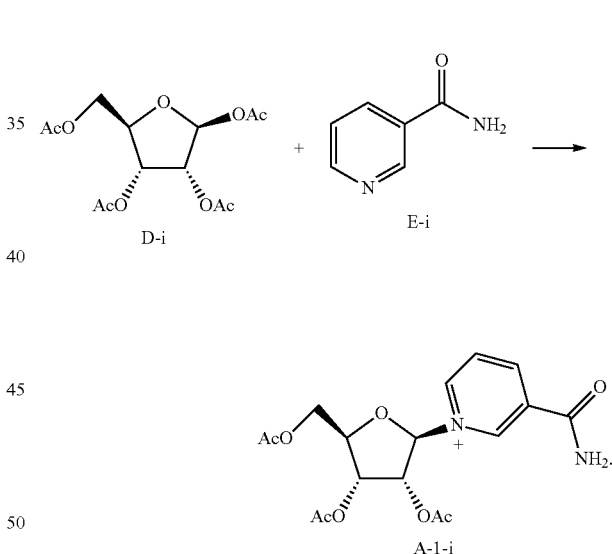

In a second step, an ammoniacal treatment of the compound of Formula (A-1-i) is carried out, leading to the compound 005:

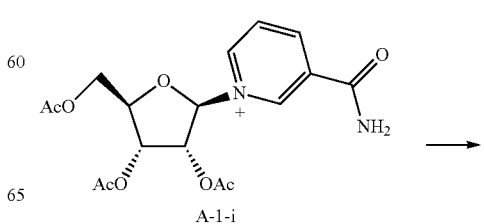

-continued

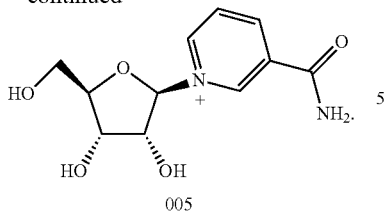

005

In a third step, the mono-phosphorylation of compound 005, in the presence of phosphoryl chloride and a trialkyl phosphate, leads to the phosphorodichloridate of Formula (B-i):

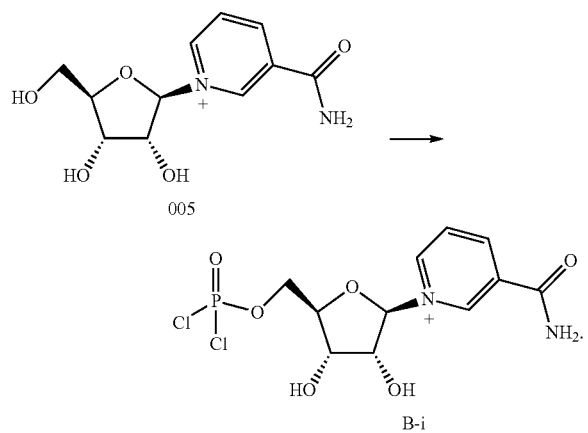

In a fourth step, the phosphorodichloridate of Formula (B-i) is hydrolyzed to yield the compound 001:

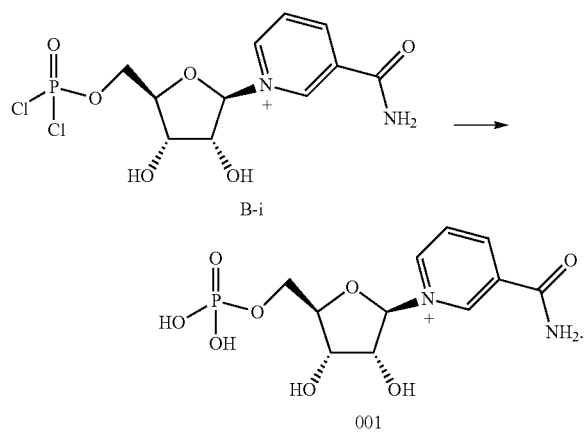

Alternatively, in a fifth step, the phosphate compound 001 obtained in the fourth step is then reacted, with the phosphorodichloridate compound of Formula (B-i) obtained as described in the third step, to give compound 009.

According to one embodiment, a step of reducing compound 005 is carried out, leading to compound 007.

The compound of formula 007 is then monophosphorylated as described in the fourth step and hydrolyzed to the compound 003.

The above method for the preparation of the compounds 001, 003, 005 and 007 can be easily adapted to the synthesis of compounds 002, 004, 006 and 008 by using the suitable starting ribose tetraacetate of Formula (D-ii):

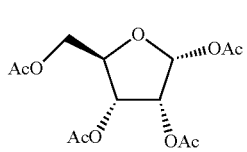

The above method for the preparation of the dimer compound 009 can be easily adapted to the synthesis of dimer compounds 010-014 by using corresponding suitable phosphorodichloridate and phosphate intermediates.

Treatment of Red Blood Cell Disorders

As mentioned above, there is an unmet need for the treatment of red blood cell disorders, especially sickle cell disease. This is thus an object of the present invention to provide a treatment of red blood cell disorders, especially sickle cell disease, for subjects in need thereof. Especially, the present invention relates to the nicotinamide mononucleotide derivatives defined hereinabove for use in the treatment of red blood cell disorders, especially sickle cell disease, in a subject in need thereof.

Red Blood Cell Disorders

In one embodiment, the present invention is thus directed to the treatment of red blood cell disorders. Non limiting examples of red blood cell disorders include anemia such as iron deficiency anemia, pernicious anemia, aplastic anemia, autoimmune hemolytic anemia; thalassemia; hemoglobin Sβ0 thalassemia; hemoglobin Sβ+ thalassemia; hemoglobin SC; hemoglobin SD; hemoglobin SE; hemoglobin SS; polycythemia vera and sickle cell disease.

According to a preferred embodiment, the blood disorder is a red blood cell disorder as described herein above.

According to a more preferred embodiment, the red blood cell disorder is sickle cell disease.

Thus, according to one embodiment, the compound of the invention as described herein above is for use in the treatment of a red blood cell disorder as described herein above.

According to a preferred embodiment, the compound of the invention as described herein above is for use in the treatment of sickle cell disease.

By "sickle cell disease" (SCD) or "drepanocytosis" it is referred to a group of inherited red blood cell disorders defined by a missense point mutation in the sequence of beta globin, which results in a glutamic acid residue at position 6 being substituted by a valine. This mutated globin, called sickle hemoglobin or hemoglobin S (HbS), aggregates and forms fibrous precipitates upon low oxygen level, leading to polymerized hemoglobin and promoting red blood cell (RBC) sickling.

Over time, patients may experience various chronic complications associated with sickle cell disease. According to one embodiment, complications associated with sickle cell disease generally involve a worsening of the disease or the development of new signs, symptoms or pathological changes that can spread throughout the body and affect other organs and can lead to the development of new diseases resulting from sickle cell disease.

Non limiting examples of complications associated with sickle cell disease include acute chest syndrome, acute pain crisis, chronic pain, delayed growth and puberty, avascular necrosis, eye problems such as retinopathy, gallstones, heart problems including coronary heart disease and pulmonary hypertension, infections such as meningitis, osteomyelitis, and sepsis; joint problems, kidney problems, leg ulcers, liver complications, pregnancy complications, priapism, severe anemia, stroke, renal necrosis or silent brain injury.

Thus, according to one embodiment, the compound of the invention as described herein above is for use in the treatment of a complication associated with sickle cell disease as described herein above.

The present invention also concerns a pharmaceutical composition comprising at least one compound for use of the invention, as described hereinabove, and at least one pharmaceutically acceptable carrier for use in the treatment of a red blood cell disorder, especially sickle cell disease.

Subjects in Need of Treatment

Preferably, the subject in need of therapeutic and/or preventive treatment is a warm-blooded animal, more preferably a human. According to one embodiment, the subject is a male. According to one embodiment, the subject is a female.

According to one embodiment, the subject is an adult, i.e. over 18 years of age. According to one embodiment, the subject is a child, i.e. under 18 years of age. According to one embodiment, the subject is an infant, i.e. having an age of more than one month and less than two years. According to one embodiment, the subject is a newborn, i.e. having an age from birth to less than one month. According to another preferred embodiment, the subject is of less than 20, 15, 10, 5 or 1 years of age. In one embodiment, the subject is of less than 18, 17, 16, 15, 14, 13, 12, 11, 10, 9, 8, 7, 6, 5, 4, 3, 2, 1 years or 5 months of ages.

According to one embodiment, the subject does not suffer from any underlying pathology.

According to one embodiment, the subject is at risk of developing a red blood cell disorder as described above. According to one embodiment, the subject is at risk of developing sickle cell disease.

According to one embodiment, the subject at risk of developing sickle cell disease belongs to an ethnic group selected from people of African descent, including African-Americans; Hispanic-Americans from Central and South America; People of Middle Eastern, southern European, Asian, Indian, and Mediterranean descent.

According to one embodiment, the subject in need of therapeutic and/or preventive treatment is diagnosed by a health professional. For example, sickle cell disease may be diagnosed by various screening test routinely carried out in the medical setting, including newborn or prenatal screening, and aim to identify if the subject has abnormal hemoglobin genes in their red blood cells.

Therapeutic Effect

According to one embodiment, the use of a nicotinamide mononucleotide derivative as described above prevents, reduces, alleviates, and/or slows down (lessens) one or more of the symptoms of a red blood cell disorder and/or complications thereof.

In a preferred embodiment, the use of a nicotinamide mononucleotide derivative as described above prevents, reduces, alleviates, and/or slows down (lessens) one or more of the symptoms of sickle cell disease (SCD) and/or complications associated with sickle cell disease, in a subject in need thereof.

In one embodiment, the symptoms of SCD include, without being limited to, recurrent acute pain crises, vaso-occlusive crises (VOCs), vascular obstruction, ischemia, intravascular hemolysis, extravascular hemolysis, hemolytic anemia, vascular obstruction, and vascular proliferative lesions.

In one embodiment, the use of a nicotinamide mononucleotide derivative as described above prevents, reduces, alleviates, and/or slows down (lessens) the sickling of the red blood cell (RBC).

In one embodiment, the use of a nicotinamide mononucleotide derivative as described above prevents, reduces, alleviates, and/or slows down (lessens) the loss of deformability of the RBC usually observed in SCD.

In one embodiment, the use of a nicotinamide mononucleotide derivative as described above prevents, reduces, alleviates, and/or slows down (lessens) the shortening of lifespan of the RBC leading usually observed in SCD.

In one embodiment, the use of a nicotinamide mononucleotide derivative as described above prevents, reduces, alleviates, and/or slows down (lessens) the sticking of RBC surface usually observed in SCD.

Over time, patients may experience various chronic complications associated with sickle cell disease. According to one embodiment, complications associated with sickle cell disease generally involve a worsening of the disease or the development of new signs, symptoms or pathological changes that can spread throughout the body and affect other organs and can lead to the development of new diseases resulting from sickle cell disease.

In one embodiment, the complications associated with SCD include acute and chronic complications. Acute complications include serious infections such as meningitis, osteomyelitis, and sepsis, and noninfectious complications such as stroke, renal necrosis, priapism. Acute chest syndrome is a potentially life-threatening complication that can involve chest pain and shortness of breath among other symptoms; some episodes of acute chest syndrome are triggered by infection. Chronic complications can emerge across multiple organs and include neurocognitive impairment, chronic kidney injury, delayed puberty, avascular necrosis, retinopathy, pulmonary hypertension, skin ulcers, and chronic pain. Individuals with SCD face ongoing and evolving lifelong difficulties as a result of their disease.

In one embodiment, the complications associated with SCD include acute chest syndrome, acute pain crisis, chronic pain, delayed growth and puberty, avascular necrosis, eye problems such as retinopathy, gallstones, heart problems including coronary heart disease and pulmonary hypertension, infections such as meningitis, osteomyelitis, and sepsis; joint problems, kidney problems, leg ulcers, liver complications, pregnancy complications, priapism, severe anemia, stroke, renal necrosis or silent brain injury.

Methods of Administration

The compounds of the invention as describes hereinabove, may be administered by oral, parenteral (e.g., intramuscular, intraperitoneal, intravenous, ICV, intracisternal injection or infusion, subcutaneous injection, or implant), by inhalation spray, nasal, rectal, sublingual, or topical routes of administration and may be formulated, alone or together, in suitable dosage unit formulations containing conventional non-toxic pharmaceutically acceptable carriers, adjuvants and vehicles appropriate for each route of administration. In addition to the treatment of warm-blooded animals, such as mice, rats, horses, cattle, sheep, dogs, cats, monkeys, etc., the compounds of the invention are effective for use in humans. The pharmaceutical compositions for the administration of the compounds of this invention may conveniently be presented in dosage unit form and may be prepared by any of the methods well known in the art of pharmacy. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases. As used herein, the term "composition" is intended to encompass a product comprising the specified ingredients in the specified amounts, as well as any product which results, directly or indirectly, from combination of the specified ingredients in the specified amounts.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs.

Compositions intended for oral use may be prepared according to any method known in the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material, such as glyceryl monostearate or glyceryl distearate may be employed. They may also be coated by the techniques described in the U.S. Pat. Nos. 4,256,108; 4,166,452; and 4,265,874 to form osmotic therapeutic tablets for control release. Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example sodium carboxymethylcellulose, methylcellulose, hydroxy-propylmethylcellulose, sodium alginate, polyvinylpyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol, such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin. Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents, such as those set forth above, and flavoring agents may be added to provide a palatable oral preparation. These compositions may be preserved by the addition of an anti-oxidant, such as ascorbic acid. Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

Syrups and elixirs may be formulated with sweetening agents, for example glycerol, propylene glycol, sorbitol or sucrose. Such formulations may also contain a demulcent, a preservative and flavouring and colouring agents.

The pharmaceutical compositions may be in the form of a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or diglycerides. In addition, fatty acids, such as oleic acid find use in the preparation of injectables. The compounds of the present invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols. For topical use, creams, ointments, jellies, solutions or suspensions, etc., containing the compounds of the present invention are employed. (For purposes of this application, topical application shall include mouthwashes and gargles.)

Dosing Regimen

In the treatment of sickle cell disease, an appropriate dosage level for the nicotinamide mononucleotide derivatives of the invention will generally be about 0.01 to 500 mg per kg patient body weight per day which can be administered in single or multiple doses. Preferably, the dosage level will be about 0.1 to about 350 mg/kg per day; more preferably about 0.5 to about 100 mg/kg per day. A suitable dosage level may be about 0.01 to 250 mg/kg per day, about 0.05 to 100 mg/kg per day, or about 0.1 to 50 mg/kg per day. Within this range the dosage may be 0.05 to 0.5, 0.5 to 5 or 5 to 50 mg/kg per day. For oral administration, the compositions are preferably provided in the form of tablets containing 1.0 to 1000 milligrams of the active ingredient, particularly 1.0, 5.0, 10.0, 15.0, 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient for the symptomatic adjustment of the dosage to the patient to be treated.

According to one embodiment, the subject in need thereof receives a treatment of at least one nicotinamide mononucleotide derivative as described above at a cumulative dose, preferably an annual at a cumulative dose, of greater than 100 mg/kg, 200 mg/kg, 300 mg/kg, 400 mg/kg, 500 mg/kg, 600 mg/kg, 700 mg/kg, 800 mg/kg, 900 mg/kg or 1000 mg/kg. In one embodiment, the subject in need receives a treatment of nicotinamide mononucleotide derivative as described above as described above at a cumulative dose, preferably an annual at a cumulative dose, of greater than 400 mg/kg, 500 mg/kg, 600 mg/kg, 700 mg/kg, 800 mg/kg, 900 mg/kg or 1000 mg/kg.

The nicotinamide mononucleotide derivative may be administered on a regimen of 1 to 4 times per day, preferably once, twice or three times per day. It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

Monotherapy/Combination Therapy

The nicotinamide mononucleotide derivatives of the invention may be used in monotherapy or in combination therapy in a subject in need of therapeutic and/or preventive treatment. Thus, according to a first embodiment, the compound for use of the invention is administered to the subject without any other active ingredient. According to a second embodiment, the compound for use of the invention is administered to the subject in combination with at least one additional active ingredient, e.g., an active ingredient as described hereinabove.

In one embodiment, the compound is administrated to the subject sequentially, simultaneously and/or separately with the other active ingredient.

In one embodiment, the other active ingredient is selected from natural extracts; opioid or non-opioid analgesics; NSAIDS; antidepressants; anticonvulsants; antibiotics; antioxidant such as CoQ10 and PQQ; hydroxyurea, L-glutamine, Kynurenine, kynurenic acid, tryptophan, Voxelotor and Crizanlizumab.

According to one embodiment, the pharmaceutical composition of the invention further comprises at least another active ingredient. According to one embodiment, the pharmaceutical composition for use of the invention comprises, in addition to the at least one compound for use of the invention, at least one additional active ingredient, e.g., an active ingredient selected from natural extracts; opioid or non-opioid analgesics; NSAIDS; antidepressants; anticonvulsants; antibiotics; antioxidant such as CoQ10 and PQQ; hydroxyurea, L-glutamine, Kynurenine, kynurenic acid, tryptophan, Voxelotor and Crizanlizumab.

According to one embodiment, the compound of the invention is used in combination with blood transfusion, especially red blood cell transfusion. In one embodiment, the compound of the invention is administrated to the subject sequentially, simultaneously and/or separately with the blood transfusion.

Kit of Parts

Another object of the invention is a kit-of-parts comprising a first part comprising a compound of the invention as described hereinabove, and a second part comprising another active ingredient, e.g., an active ingredient selected from, but not limited to, a natural extract; opioid or non-opioid analgesics; NSAIDS; antidepressants; anticonvulsants; antibiotics; antioxidant such as CoQ10 and PQQ; hydroxyurea, L-glutamine, Kynurenine, kynurenic acid, tryptophan, Voxelotor and Crizanlizumab.

In one embodiment, the kit-of-parts of the invention comprises a first part comprising compounds 001-014, or a pharmaceutically acceptable salt or solvate thereof, and a second part comprising another active ingredient, e.g., an active ingredient as described hereinabove.

Method of Treatment

This invention also relates to the use of a compound of invention or a pharmaceutical composition as described hereinabove in the treatment of a red blood cell disorder as described hereinabove.

This invention also relates to the use of a compound of the invention or a pharmaceutical composition as described hereinabove in the manufacture of a medicament for the treatment of a red blood cell disorder as described hereinabove.

This invention also relates to a method for the treatment of a red blood cell disorder as described hereinabove in a subject in need thereof, comprising a step of administrating to said subject a therapeutically effective amount of a compound of the invention or a pharmaceutical composition as described hereinabove.

EXAMPLES

Figure 1:
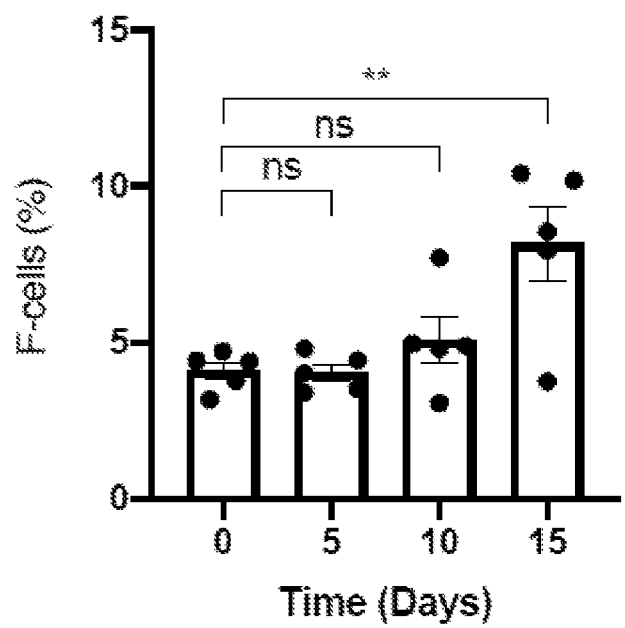
FIG. 1 is a histogram showing the percentage of F-cells overtime in presence of compound 001, using antibodies against fetal hemoglobin by flow cytometry (FACS).

The present invention is further illustrated by the following examples.

Example 1: Synthesis of Compounds of the Invention

Materials and Methods

All materials were obtained from commercial suppliers and used without further purification. Thin-layer chromatography was performed on TLC plastic sheets of silica gel 60F254 (layer thickness 0.2 mm) from Merck. Column chromatography purification was carried out on silica gel 60 (70-230 mesh ASTM, Merck). Melting points were determined either on a digital melting point apparatus (Electrothermal IA 8103) and are uncorrected or on a Kofler bench type WME (Wagner & Munz). IR, $^1$H, $^{19}$F and $^{13}$C NMR spectra confirmed the structures of all compounds. IR spectra were recorded on a Perkin Elmer Spectrum 100 FT-IR spectrometer and NMR spectra were recorded, using CDCl$_3$, CD$_3$CN, D$_2$O or DMSO-d$_6$ as solvent, on a Bruker AC 300, Advance DRX 400 and Advance DRX 500 spectrometers, for $^1$H, 75 or 100 MHz for $^{13}$C and 282 or 377 MHz for $^{19}$F spectra. Chemical shifts (δ) were expressed in parts per million relative to the signal indirectly (i) to CHCl$_3$ (δ 7.27) for $^1$H and (ii) to CDCl$_3$ (δ 77.2) for $^{13}$C and directly (iii) to CFCl$_3$ (internal standard) (δ 0) for $^{19}$F. Chemical shifts are given in ppm and peak multiplicities are designated as follows: s, singlet; br s, broad singlet; d, doublet; dd, doublet of doublet; t, triplet; q, quadruplet; quint, quintuplet; m, multiplet. The high-resolution mass spectra (HRMS) were obtained from the "Service central d'analyse de Solaize" (Centre national de la recherche scientifique) and were recorded on a Waters spectrometer using electrospray-TOF ionization (ESI-TOF).

General Experimental Procedures

Step 1: Synthesis of the Compound of Formula A-1

The compound of formula D (1.0 equiv.) is dissolved in dichloromethane. Nicotinamide of formula E (1.50 equiv.) and TMSOTf (1.55 equiv.) are added at room temperature. The reaction mixture is heated under reflux and stirred until the reaction is complete. The mixture is cooled to room temperature and filtered. The filtrate is concentrated to dryness to give tetraacetate A-1.

Step 2: Synthesis of the Compound of Formula A-2

Tetraacetate A-1 is dissolved in methanol and cooled to −10° C. Ammonia 4.6 M in methanol (3.0 equivalents) at −10° C. is added and the mixture is stirred at this temperature until the reaction is complete. Dowex HCR (H+) resin is added up to pH 6-7. The reaction mixture is heated to 0° C. and filtered. The resin is washed with a mixture of methanol and acetonitrile. The filtrate is concentrated to dryness. The residue is dissolved in the acetonitrile and concentrated to dryness. The residue is dissolved in the acetonitrile to give a solution of the compound of formula A-2.

Step 3: Synthesis of the Compound of Formula A-3

The solution of the crude compound of formula A-2 in acetonitrile is diluted with trimethyl phosphate (10.0 equivalents). The acetonitrile is distilled under vacuum and the mixture is cooled to −10° C. Phosphorus oxychloride (4.0 equivalents) is added at 10° C. and the mixture is stirred at 10° C. until the reaction is complete.

Steps 4 and 5: Synthesis of the Compound of Formula 001

The mixture obtained in step 3 above is hydrolyzed by the addition of a 50/50 mixture of acetonitrile and water, followed by the addition of methyl tert-butyl ether. The mixture is filtered and the solid is dissolved in water. The aqueous solution is neutralized by the addition of sodium bicarbonate and extracted with dichloromethane. The aqueous layer is concentrated to dryness to yield the crude formula 001 compound, which is purified on a DOWEX 50wx8 column with elution in water followed by a silica gel chromatographic column.

Step 4 and Step 5: Synthesis of Compound of Formula 009

The mixture is hydrolyzed by addition of a 50/50 mixture of acetonitrile and water, followed by addition of tert-butyl methyl ether. The mixture is filtered and the solid is dissolved in water. The aqueous solution is neutralized by addition of sodium bicarbonate and extracted with dichloromethane. The aqueous layer is concentrated to dryness to give a crude mixture of NMN and di-NMN of formula 009. Isolation of Di-NMN of Formula 009:

NMN and di-NMN of formula 009 are separated by purification on Dowex 50wx8 with water elution. The fractions containing di-NMN are concentrated to dryness. The residue is purified by column chromatography on silica gel (gradient isopropanol/water). Pure fractions are combined and concentrated. The residue is freeze-dried to afford di-NMN as a beige solid.

$^{31}$P RMN: δ (ppm, reference 85% H$_3$PO$_4$: 0 ppm dans D$_2$O)=−11.72; $^1$H RMN: δ (ppm, reference TMS: 0 ppm dans D$_2$O)=4.20 (ddd, $J_{H-H}$=11.9, 3.5, 2.4 Hz, 2H), 4.35 (ddd, $J_{H-H}$=11.9, 3.9, 2.2 Hz, 2H), 4.43 (dd, $J_{H-H}$=5.0, 2.6 Hz, 2H), 4.53 (t, $J_{H-H}$=5.0 Hz, 2H), 4.59 (m, 2H), 6.16 (d, $J_{H-H}$=5.4 Hz, 2H), 8.26 (dd, $J_{H-H}$=8.1, 6.3 Hz, 2H), 8.93 (d, $J_{H-H}$=8.1 Hz, 2H), 9.25 (d, $J_{H-H}$=6.2 Hz, 2H), 9.41 (s, 2H); $^{13}$C RMN: δ (ppm, reference TMS: 0 ppm dans D$_2$O)=64.84 (CH$_2$), 70.73 (CH), 77.52 (CH), 87.11 (CH), 99.88 (CH), 128.65 (CH), 133.89 (Cq), 139.84 (CH), 142.54 (CH), 146.04 (CH), 165.64 (Cq); MS (ES+): m/z=122.8 [Mnicotinamide+H]+, 650.8 [M+H]+.

Synthesis of Compound of Formula 010

Phosphorus oxychloride (3.0 eq.) is added to trimethylphosphate (20.0 eq.) at −5° C. β-NR chloride (1.0 eq.) is added by portions at −5° C. and the reaction mixture stirred overnight at −5° C. Morpholine (3.0 eq.) is added dropwise at −10/0° C. and the mixture stirred for 2-3 h. a-NMN (1.0 eq.) is then added by portions at −5° C. and the reaction mixture stirred at −5° C. overnight. Hydrolysis is performed by dropwise addition of water (5 vol.) at −10/0° C. and the mixture is stirred until complete homogenization at 10-15° C. The reaction mixture is then extracted with dichloromethane (6*10 vol.) and the aqueous phase neutralized by eluting through Purolite A600E formate form resin (theoretical amount to neutralize HCl coming from POCl$_3$). The eluate is then concentrated on vacuum at 45/50° C. to give the crude containing the α,β-diNMN of formula 010. Elution with water through Dowex 50wx8 100-200 mesh H+ form resin allows removing of some impurities. Fractions containing compound 010 are combined and concentrated on vacuum at 45-50° C. The crude is then purified by preparative chromatography on Luna Polar RP 10 μm stationary phase with elution with a 10 mM NaH$_2$PO$_4$ aqueous solution. Pure fractions are combined and eluted with water on Purolite C$_{100}$EH H$^+$ form resin (needed quantity to fully exchange Na$^+$ by H$^+$), then eluted on Purolite A600E acetate form resin (needed quantity to fully exchange H$_2$PO$_4$$^-$ by acetate). The eluate is concentrated on vacuum and the residue freeze-dried to afford compound 010 as a white solid.

$^{31}$P RMN: δ (ppm, reference 85% H$_3$PO$_4$: 0 ppm dans D$_2$O)=−11.87, −11.69, −11.46, −11.29; $^1$H RMN: δ (ppm, reference TMS: 0 ppm dans D$_2$O)=4.10 (ddd, J=11.1, 6.1, 3.1 Hz, 1H), 4.15-4.25 (m, 2H), 4.36 (ddd, J=12.2, 4.4, 2.4 Hz, 1H), 4.40 (dd, J=4.9, 2.4 Hz, 1H), 4.44 (dd, J=5.0, 2.7 Hz, 1H), 4.53 (t, J=5.0 Hz, 1H), 4.5 (m, 1H), 4.85 (m, 1H), 4.92 (t, J=5.3 Hz, 1H), 6.15 (d, J=5.5 Hz, 1H), 6.51 (d, J=5.7 Hz, 1H), 8.14 (dd, J=8.0, 6.3 Hz, 1H), 8.26 (dd, J=8.1, 6.3 Hz, 1H), 8.88 (d, J=8.1 Hz, 1H), 8.92 (d, J=8.1 Hz, 1H), 9.02 (d, J=6.3 Hz, 1H), 9.24 (s, 1H), 9.26 (d, J=6.4 Hz, 1H), 9.40 (s, 1H); $^{13}$C RMN: δ (ppm, reference TMS: 0 ppm dans D$_2$O)=64.83, 64.87 (CH$_2$), 65.30, 65.35 (CH$_2$), 70.65 (CH), 70.74 (CH), 71.92 (CH), 77.51 (CH), 87.03, 87.10 (CH), 87.19, 87.26 (CH), 96.57 (CH), 99.83 (CH), 126.89 (CH), 128.54 (CH), 132.44 (Cq), 133.81 (Cq), 139.85 (CH), 140.92 (CH), 142.50 (CH), 143.49 (CH), 145.06 (CH), 145.97 (CH), 165.64 (Cq), 165.88 (Cq); MS (ES+): m/z=122.8 [Mnicotinamide+H]+, 650.9 [M+H]+.

Synthesis of Compound of Formula 011

Phosphorus oxychloride (3.0 eq.) is added to trimethylphosphate (20.0 eq.) at −5° C. α-NR chloride (1.0 eq.) is added by portions at −5° C. and the reaction mixture stirred overnight at −5° C. Morpholine (3.0 eq.) is added dropwise at −10/0° C. and the mixture stirred for 2-3 h. α-NMN (1.0 eq.) is then added by portions at −5° C. and the reaction mixture stirred at −5° C. overnight. Hydrolysis is performed by dropwise addition of water (5 vol.) at −10/0° C. and the mixture is stirred until complete homogenization at 10-15° C. The reaction mixture is then extracted with dichloromethane (6*10 vol.) and the aqueous phase neutralized by eluting through Purolite A600E formate form resin (theoretical amount to neutralize HCl coming from POCl$_3$). The eluate is then concentrated on vacuum at 45/50° C. to give the crude containing the α,α-diNMN of formula 011. Elution with water through Dowex 50wx8 100-200 mesh H$^+$ form resin allows removing of some impurities. Fractions containing the compound 011 are combined and concentrated on vacuum at 45-50° C. The crude is then purified by preparative chromatography on Luna Polar RP 10 μm stationary phase with elution with a 10 mM NaH$_2$PO$_4$ aqueous solution. Pure fractions are combined and eluted with water on Purolite C$_{100}$EH H$^+$ form resin (needed quantity to fully exchange Na$^+$ by H$^+$), then eluted on Purolite A600E acetate form resin (needed quantity to fully exchange H$_2$PO$_4$$^-$ by acetate). The eluate is concentrated on vacuum and the residue freeze-dried to afford compound 011 as a white solid.

$^{31}$P RMN: δ (ppm, reference 85% H$_3$PO$_4$: 0 ppm dans D$_2$O)=−11.40; $^1$H RMN: δ (ppm, reference TMS: 0 ppm dans D$_2$O)=4.14 (ddd, J=11.4, 3.4, 2.8 Hz, 2H), 4.23 (ddd, J=11.6, 3.3, 2.8 Hz, 2H), 4.44 (dd, J=4.8, 2.3 Hz, 2H), 4.88 (m, 2H), 4.96 (t, J=5.3 Hz, 2H), 6.54 (d, J=5.7 Hz, 2H), 8.15 (dd, J=8.1, 6.2 Hz, 2H), 8.89 (d, J=8.1 Hz, 2H), 9.05 (d, J=6.3 Hz, 2H), 9.26 (s, 2H); $^{13}$C RMN: δ (ppm, reference TMS: 0 ppm dans D$_2$O)=65.37 (CH2), 70.70 (CH), 71.95 (CH), 87.30 (CH), 96.62 (CH), 126.91 (CH), 132.45 (Cq), 140.94 (CH), 143.52 (CH), 145.07 (CH), 165.90 (Cq); MS (ES+): m/z=122.7[Mnicotinamide+H]+, 650.8 [M+H]+.

Example 2: Evaluation of Compounds of the Invention on Sickle Red Blood Cell Experimental Models The aim of the present study was to evaluate, the effects of i.p. daily administration of compounds 001, 010 and 011 at 185 mg/kg as modulator of red blood cell sickling and fetal hemoglobin expression in erythroid cells and its potential role in therapy for sickle cell disease on mouse model of SCD.

I. Materials and Methods

Material

Animals:

Townes S/S mice on a 129/B6 mixed genetic background.

Methods

1. Preparation of Formulation:

The powders of compounds 001, 010 and 011 (185 mg/kg) were dissolved in vehicle (the solution is used at room temperature for maximum 1 day). A fresh sample for each administration was prepared every day except the week-end (the solution is prepared on Saturday and is used on Saturday and Sunday).

2. Sickle Red Blood Cell

In Townes S/S mice, mouse alpha- and beta-globin gene loci are deleted and replaced by human alpha- and beta-globin genes. When carrying two copies of the beta S allele, mice develop a human sickle disease phenotype with sickle-shaped red blood cells are seen in blood smears.

3. Experimental Groups

Group Description:

Group 1: Vehicle (i.p.)
Group 2: compound 001 (185 mg/kg)
Group 3 compound 010 (185 mg/kg)
Group 4: compound 011 (185 mg/kg)

4. Treatment

Mice were i.p treated with compounds 001, 010 and 011 during all the experiment (D0 to D15) once per day. Last injection occurred 24 hours before sacrifice.

5. Blood Collection

Retro-orbital blood collection was performed at the inclusion D0 and at D5, D10 and D15 through facial vein bleeding.

6. Ex-Vivo

Ex-vivo blood collected were assessed for percentage of F-cells using antibodies against fetal hemoglobin by FACS and reticulocyte counts using reticount by FACS. Red blood cells sickling was assessed under hypoxia.

II. Results and Discussion

1. Percentage of F-Cells

FIG. 1 shows the percentage of F-cells using antibodies against fetal hemoglobin by FACS.

The results show that treatment with:

Compound 001 (185 mg/kg/d, i.p.) led to a significant increase of the mean F-cells from less than 5% to 8% over the 15 days treatment of mice (FIG. 1);

2. Reticulocyte Counts Using Reticount

Figure 2:
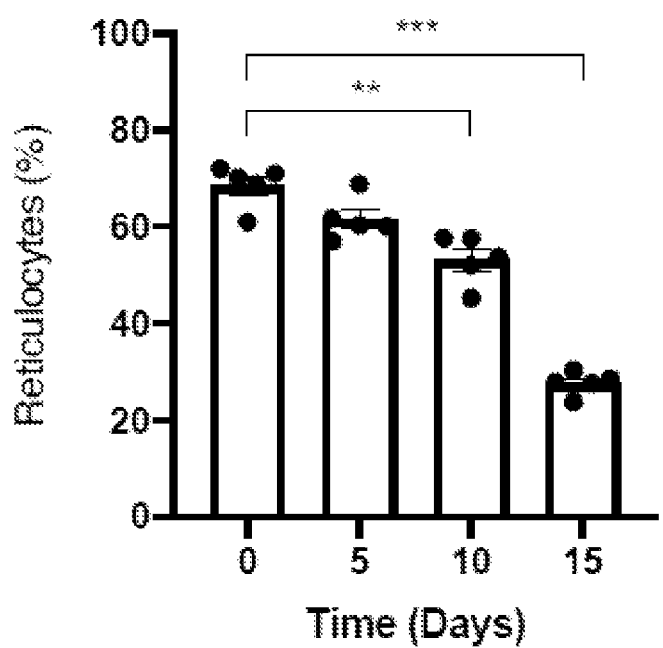
FIG. 2 is a histogram showing the reticulocyte counts overtime in presence of compound 001, using Reticount by FACS.

FIG. 2 shows the reticulocyte counts using Reticount by FACS.

The results show that treatment with:

Compound 001 (185 mg/kg/d, i.p.) led to a significant decrease of the percentage of reticulocytes from 70% to 30% over the 15 days treatment of mice (FIG. 2);

3. RBC Sickling Under Hypoxia Ex Vivo

Figure 3:
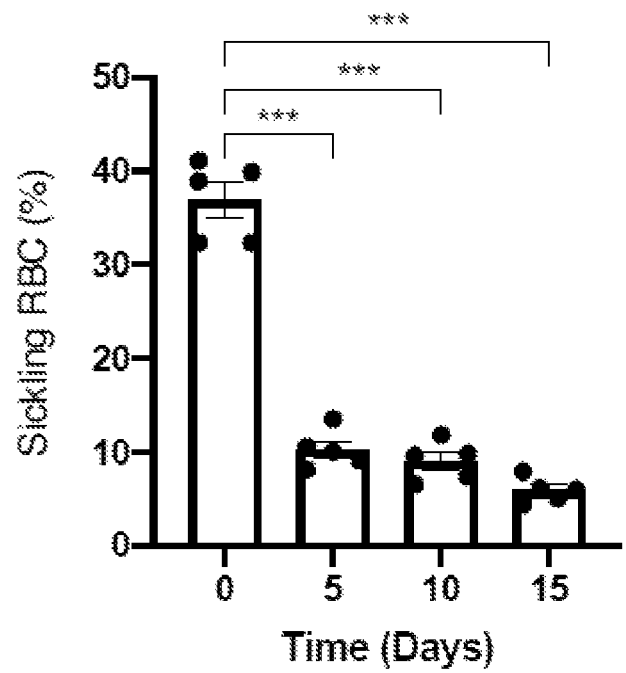
FIG. 3 is a histogram showing the ability of compound 001 to prevent sickling of SS RBCs at a 1% $O_2$ overtime. Non-parametric one-way ANOVA followed by Kruskal-Wallis test: *$p<0.05$; $p<0.01$; *$p<0.001$; ****$p<0.0001$.
Figure 4:
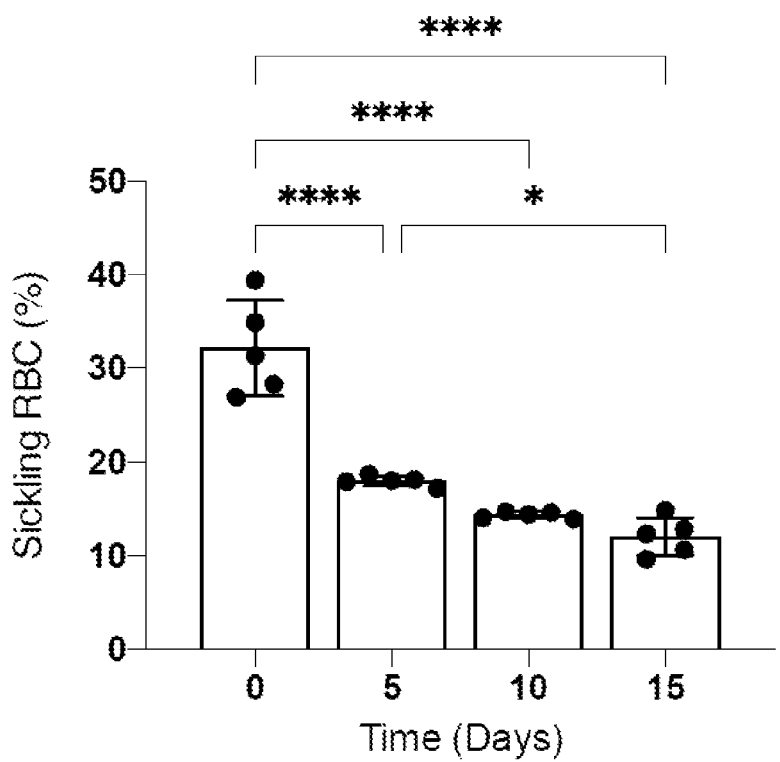
FIG. 4 is a histogram showing the ability of compound 010 to prevent sickling of SS RBCs at a 1% $O_2$ overtime. Non-parametric one-way ANOVA followed by Kruskal-Wallis test: *$p<0.05$; $p<0.01$; *$p<0.001$; ****$p<0.0001$.
Figure 5:
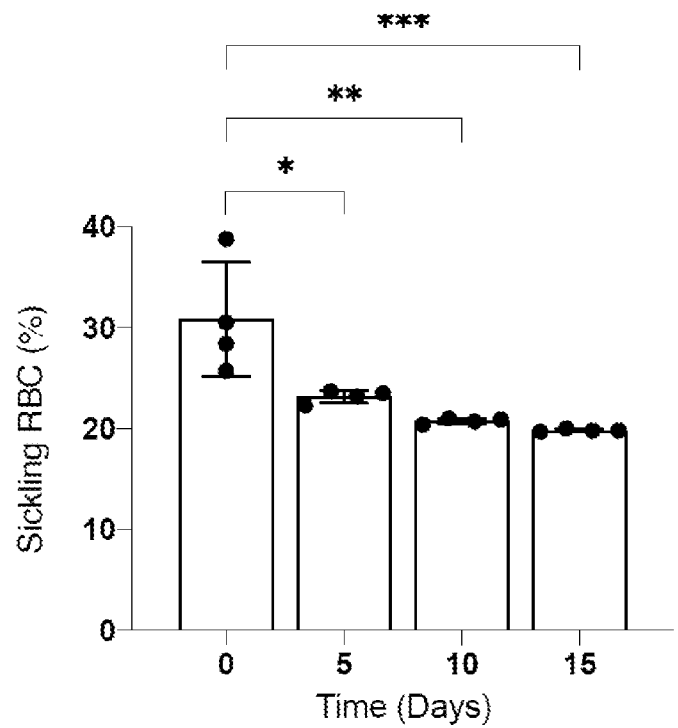
FIG. 5 is a histogram showing the ability of compound 011 to prevent sickling of SS RBCs at a 1% $O_2$ overtime. Non-parametric one-way ANOVA followed by Kruskal-Wallis test: *$p<0.05$; $p<0.01$; *$p<0.001$; ****$p<0.0001$.

FIGS. 3, 4 and 5 show the ability of compounds 001 (FIG. 3), 010 (FIG. 4) and 011 (FIG. 5) to prevent sickling of SS RBCs at a 1% $O_2$.

SS RBCs from treated mice and collected at D0, D5, D10 and D15 were submitted to hypoxia for 30 minutes in a hypoxic chamber (1% $O_2$). Percentage of sickling RBCs was then assessed for each time point with compounds 001, 010 and 011.

The results showed that treatment with:
- Compound 001 (185 mg/kg/d, i.p.) led to a significant (p<0.001) decrease of the percentage of sickling cells from 40% at D0 to less than 10% after 15 days treatment of mice (FIG. 4).
- Compound 010 (185 mg/kg/d, i.p.) led to a significant decrease (p<0.0001) of the percentage of sickling cells from 32% at D0 to less than 15% after 15 days treatment of mice.
- Compound 011 (185 mg/kg/d, i.p.) led to a significant decrease (p<0.001) of the percentage of sickling cells from 31% at D0 to 20% after 15 days treatment of mice.

III. Conclusion

These results indicate that treatments with compounds 001, 010 and/or 011 reduce red blood cell sickling under hypoxia and increase the proportion of circulating erythroid cells expressing fetal hemoglobin, illustrating their potential role in therapy for sickle cell disease.

Example 3: Comparison of the Efficacy of NMN (Compound 001) Vs L-Glutamine on Sickle Red Blood Cell Experimental Model The purpose of this study is to evaluate the effects of i.p. daily administration of compound 001 at 185 mg/kg and/or L-Glutamine (L-Gln) at 180 mg/Kg on hematological parameters and RBC sickling. L-Gln has received approval by the FDA for the treatment of sickle cell disease (SCD) patients in the United States as it has been shown that L-Gln administration reduces the severity and frequency of VOCs.

I. Materials and Methods

Animals

Townes S/S mice on a 129/B6 mixed genetic background aged 8-12 weeks.

Methods

1. Preparation of Formulation:

The powder of compound 001 (185 mg/kg) was dissolved in vehicle (the solution is used at room temperature for maximum 1 day). The powder of L-Glutamine (180 mg/kg) was dissolved in vehicle (the solution is used at room temperature for maximum 1 day). A fresh sample for each administration was prepared every day except the weekend (the solution is prepared on Saturday and is used on Saturday and Sunday).

2. Sickle Red Blood Cell

In Townes S/S mice, mouse alpha- and beta-globin gene loci are deleted and replaced by human genes coding for the alpha- and beta-globin. When carrying two copies of the beta S allele, mice develop a human sickle disease phenotype with sickle-shaped red blood cells are seen in blood smears.

3. Experimental Groups

Group Description:
- Group 1: Vehicle PBS (i.p.)
- Group 2: Compound 001 (185 mg/kg)
- Group 3 L-Gln (180 mg/kg)
- Group 4: Compound 001 (185 mg/kg)+L-Gln (180 mg/kg)

4. Treatment

Mice were i.p treated with Compound 001, L-Gln or the combination of compound 001+L-Gln during all the experiment (D0 to D15) once per day. Last injection occurred 24 hours before sacrifice.

5. Blood Collection

Retro-orbital blood collection was performed at the inclusion and at D15.

6. Ex-Vivo

Ex-vivo blood collected were assessed for blood parameters and RBC sickling ex vivo under normoxia (20% $O_2$) and hypoxia (1% $O_2$ for 0.5 hour).

II. Results and Discussion

1. Red Blood Cells

Figure 6:
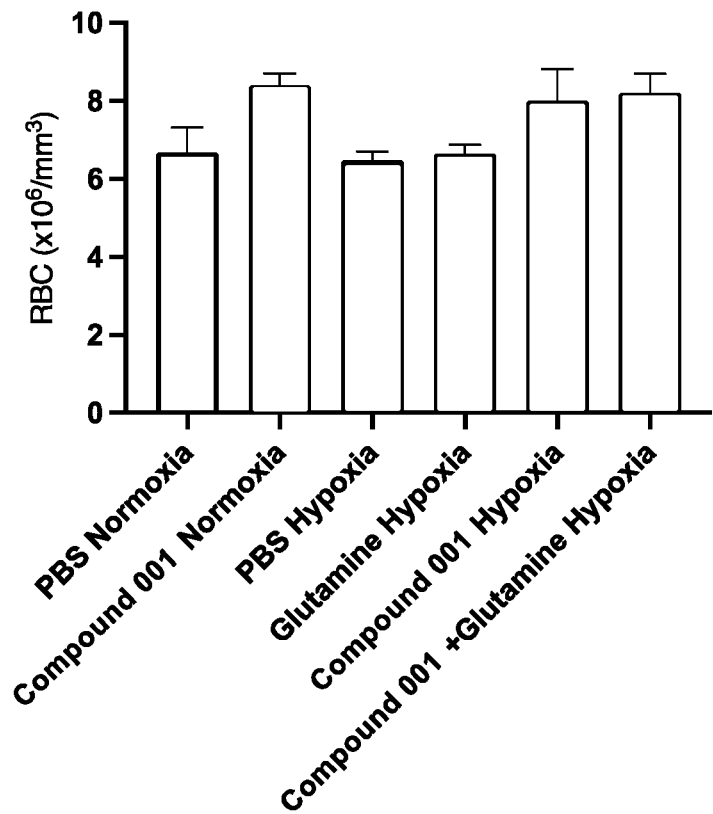
FIG. 6 is a histogram showing the concentration of red blood cells in the blood of SCD-model mice treated with compound 001, L-Glutamine (L-Gln) or a combination of compound 001+L-glutamine, under normoxia or hypoxia.

FIG. 6 shows concentration of red blood cells in blood of animals treated with compound 001, L-Gln or compound 001+L-glutamine, under normoxia or hypoxia.

The results show that treatment with:
- L-Gln did not affect the concentration of RBC under normoxia or hypoxia.
- Compound 001 (185 mg/kg/d, i.p.) led to a significant increase of RBC concentration both under normoxia and hypoxia, compared to Vehicle or L-Gln. Hypoxia did not result in a decrease of RBC in blood of mice treated with compound 001.
- The combination of compound 001 and L-Gln does not improve the results obtained with compound 001 alone.

2. Hemoglobin Concentration

Figure 7:
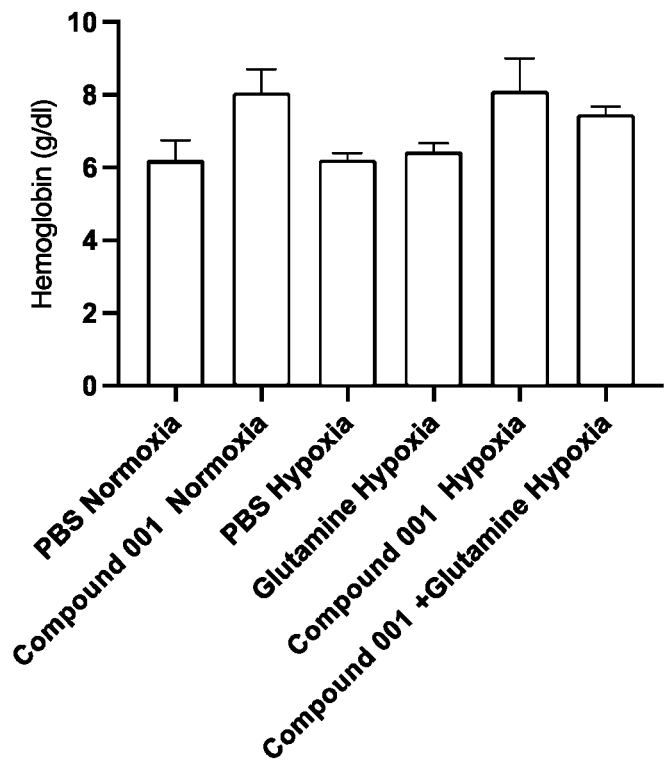
FIG. 7 is a histogram showing the hemoglobin concentration in the blood of SCD-model mice treated with compound 001, L-Glutamine (L-Gln) or a combination of compound 001+L-glutamine, under normoxia or hypoxia.

FIG. 7 shows hemoglobin concentration in blood of animals treated with compound 001, L-Gln or compound 001+L-glutamine, under normoxia or hypoxia.

The results show that treatment with:
- L-Gln did not affect hemoglobin concentration vs vehicle under normoxia or hypoxia.
- Compound 001 (185 mg/kg/d, i.p.) led to a significant increase of hemoglobin concentration both under normoxia and hypoxia, compared to Vehicle or L-Gln. Hypoxia did not result in a decrease of hemoglobin in blood of mice treated with compound 001.
- The combination of compound 001 and L-Gln does not improve the results obtained with compound 001 alone.

3. Hematocrit Percentage

Figure 8:
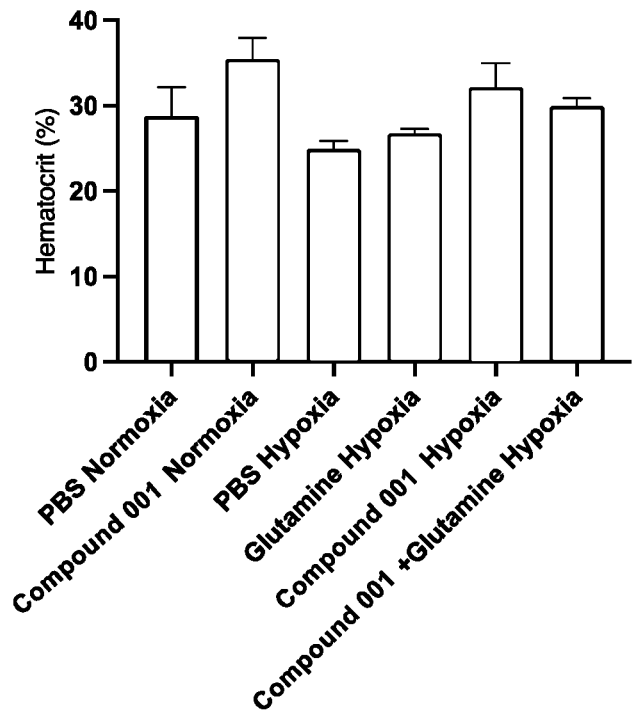
FIG. 8 is a histogram showing the hematocrit percentage in the blood of SCD-model mice treated with compound 001, L-Glutamine (L-Gln) or a combination of compound 001+L-glutamine, under normoxia or hypoxia.

FIG. 8 shows hematocrit percentage in blood of animals treated with compound 001, L-Gln or compound 001+L-glutamine, under normoxia or hypoxia.

The results show that treatment with:
- L-Gln did not affect hematocrit percentage vs vehicle under normoxia or hypoxia.
- Compound 001 (185 mg/kg/d, i.p.) led to a significant increase of hemtocrit percentage both under normoxia and hypoxia, compared to Vehicle or L-Gln. Hypoxia did not result in a decrease of hematocrit percentage in blood of mice treated with compound 001.
- The combination of compound 001 and L-Gln does not improve the results obtained with compound 001 alone.

III. Conclusion

Therefore, it was demonstrated that the compound of formula I according to the invention can increase the amount of RBC, the concentration of hemoglobin and percentage hematocrit in the blood of a subject, especially a subject having sickle cell disease, in both normoxic and hypoxic conditions. The compound of the invention is thus at least as efficient as L-Gln, the standard of care in the USA for sickle cell disease.

The invention claimed is:
1. A method of treatment of Polycythemia comprising the administration of a compound of Formula (I),

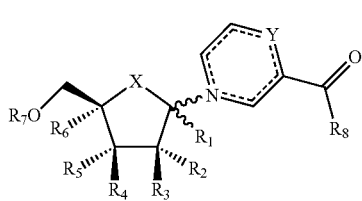

or a pharmaceutically acceptable salt or solvate thereof; wherein:

X is selected from O, $CH_2$, S, Se, CHF, $CF_2$ and $C=CH_2$;

$R_1$ is selected from H, azido, cyano, $(C_1-C_8)$alkyl, $(C_1-C_8)$thio-alkyl, $(C_1-C_8)$heteroalkyl and OR; wherein R is selected from H and $(C_1-C_8)$alkyl;

$R_2$, $R_3$, $R_4$ and $R_5$ are independently selected from H, halogen, azido, cyano, hydroxyl, $(C_1-C_{12})$alkyl, $(C_1-C_{12})$thio-alkyl, $(C_1-C_{12})$heteroalkyl, $(C_1-C_{12})$haloalkyl and OR; wherein R is selected from H, $(C_1-C_{12})$alkyl, $-C(O)(C_1-C_{12})$alkyl, $-C(O)NH(C_1-C_{12})$alkyl, $-C(O)O(C_1-C_{12})$alkyl, $-C(O)$aryl, $-C(O)(C_1-C_{12})$alkyl-$(C_5-C_{12})$aryl, $-C(O)NH(C_1-C_{12})$alkyl-$(C_5-C_{12})$aryl, $-C(O)O(C_1-C_{12})$alkyl-$(C_5-C_{12})$aryl and $-C(O)CHR_{AA}NH_2$; wherein $R_{AA}$ is a side chain selected from a proteinogenic amino acid;

$R_6$ is selected from H, azido, cyano, $(C_1-C_8)$alkyl, $(C_1-C_8)$thio-alkyl, $(C_1-C_8)$heteroalkyl and OR; wherein R is selected from H and $(C_1-C_8)$alkyl;

$R_7$ is selected from $P(O)R_9R_{10}$, $P(S)R_9R_{10}$ and

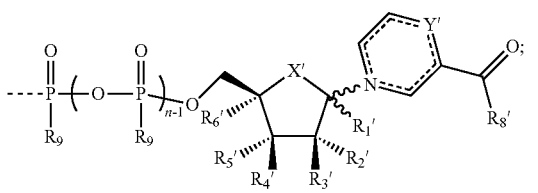

wherein:

$R_9$ and $R_{10}$ are independently selected from OH, $OR_{11}$, $NR_{13}R_{14}$, $(C_1-C_8)$alkyl, $(C_2-C_8)$alkenyl, $(C_2-C_8)$alkynyl, $(C_3-C_{10})$cycloalkyl, $(C_5-C_{12})$aryl, $(C_5-C_{12})$aryl-$(C_1-C_8)$alkyl, $(C_1-C_8)$alkyl-$(C_5-C_{12})$aryl, $(C_1-C_8)$heteroalkyl, $(C_3-C_8)$heterocycloalkyl, $(C_5-C_{12})$heteroaryl and $NHCR_{\alpha}R_{\alpha'}C(O)OR_{12}$; wherein:

$R_{11}$ is selected from $(C_1-C_{10})$alkyl, $(C_3-C_{10})$cycloalkyl, $(C_5-C_{12})$aryl, $(C_1-C_{10})$alkyl-$(C_5-C_{12})$aryl, substituted $(C_5-C_{12})$aryl, $(C_1-C_{10})$heteroalkyl, $(C_1-C_{10})$haloalkyl, $-(CH_2)_mC(O)(C_1-C_{15})$alkyl, $-(CH_2)_mOC(O)(C_1-C_{15})$alkyl, $-(CH_2)_mOC(O)O(C_1-C_{15})$alkyl, $-(CH_2)_mSC(O)(C_1-C_{15})$alkyl, $-(CH_2)_mC(O)O(C_1-C_{15})$alkyl, $-(CH_2)_mC(O)O(C_1-C_{15})$alkyl-$(C_5-C_{12})$aryl; wherein m is an integer selected from 1 to 8; and $-P(O)(OH)OP(O)(OH)_2$; and an internal or external counterion;

$R_{12}$ is selected from hydrogen, $(C_1-C_{10})$alkyl, $(C_2-C_8)$alkenyl, $(C_2-C_8)$alkynyl, $(C_1-C_{10})$haloalkyl, $(C_3-C_{10})$cycloalkyl, $(C_3-C_{10})$heterocycloalkyl, $(C_5-C_{12})$aryl, $(C_1-C_4)$alkyl-$(C_5-C_{12})$aryl and $(C_5-C_{12})$heteroaryl; wherein said aryl or heteroaryl groups are optionally substituted by one or two groups selected from halogen, trifluoromethyl, $(C_1-C_6)$alkyl, $(C_1-C_6)$alkoxy and cyano;

$R_{13}$ and $R_{14}$ are independently selected from H, $(C_1-C_8)$alkyl and $(C_1-C_8)$alkyl-$(C_5-C_{12})$aryl; and $R_{\alpha}$ and $R_{\alpha'}$ are independently selected from an hydrogen, $(C_1-C_{10})$alkyl, $(C_2-C_{10})$alkenyl, $(C_2-C_{10})$alkynyl, $(C_3-C_{10})$cycloalkyl, $(C_1-C_{10})$thio-alkyl, $(C_1-C_{10})$hydroxyalkyl, $(C_1-C_{10})$alkyl-$(C_5-C_{12})$aryl, $(C_5-C_{12})$aryl, $-(CH_2)_3NHC(=NH)NH_2$, (1H-indol-3-yl)methyl, (1H-imidazol-4-yl)methyl and a side chain selected from a proteinogenic or non-proteinogenic amino acid; wherein said aryl groups are optionally substituted with a group selected from hydroxyl, $(C_1-C_{10})$alkyl, $(C_1-C_6)$alkoxy, halogen, nitro and cyano; or $R_9$ and $R_{10}$ together with the phosphorus atom to which they are attached form a 6-membered ring wherein $-R_9-R_{10}-$ represents $-O-CH_2-CH_2-CHR-O-$; wherein R is selected from hydrogen, $(C_5-C_6)$aryl and $(C_5-C_6)$heteroaryl; wherein said aryl or heteroaryl groups are optionally substituted by one or two groups selected from halogen, trifluoromethyl, $(C_1-C_6)$alkyl, $(C_1-C_6)$alkoxy and cyano;

X' is selected from O, $CH_2$, S, Se, CHF, $CF_2$ and $C=CH_2$;

$R_{1'}$ is selected from H, azido, cyano, $(C_1-C_8)$alkyl, $(C_1-C_8)$thio-alkyl, $(C_1-C_8)$heteroalkyl and OR; wherein R is selected from H and $(C_1-C_8)$alkyl;

$R_{2'}$, $R_{3'}$, $R_{4'}$ and $R_{5'}$ are independently selected from H, halogen, azido, cyano, hydroxyl, $(C_1-C_{12})$alkyl, $(C_1-C_{12})$thio-alkyl, $(C_1-C_{12})$heteroalkyl, $(C_1-C_{12})$haloalkyl and OR; wherein R is selected from H, $(C_1-C_{12})$alkyl, $-C(O)(C_1-C_{12})$alkyl, $-C(O)NH(C_1-C_{12})$alkyl, $-C(O)O(C_1-C_{12})$alkyl, $-C(O)$aryl, $-C(O)(C_1-C_{12})$alkyl-$(C_5-C_{12})$aryl, $-C(O)NH(C_1-C_{12})$alkyl-$(C_5-C_{12})$aryl, $-C(O)O(C_1-C_{12})$alkyl-$C_8-C_{12}$aryl and $-C(O)CHR_{AA}NH_2$; wherein $R_{AA}$ is a side chain selected from a proteinogenic amino acid;

$R_{6'}$ is selected from H, azido, cyano, $(C_1-C_8)$alkyl, $(C_1-C_8)$thio-alkyl, $(C_1-C_8)$heteroalkyl and OR; wherein R is selected from H and $(C_1-C_8)$alkyl;

$R_{8'}$ is selected from H, OR, $NR_{15}R_{16'}$, NH—$NHR_{15'}$, SH, CN, $N_3$ and halogen; wherein R is selected from H and $(C_1-C_8)$alkyl, and $R_{15'}$ and $R_{16'}$ are independently selected from H, $(C_1-C_8)$alkyl, $(C_1-C_8)$alkyl-$(C_5-C_{12})$aryl and $-CHR_{AA'}CO_2H$ wherein $R_{AA'}$ is a side chain selected from a proteinogenic or non-proteinogenic amino acid;

Y' is selected from CH, $CH_2$, $CHCH_3$, $C(CH_3)_2$ and $CCH_3$;

n is an integer selected from 1 to 3;

- - - represents the point of attachment;

= represents a single or double bond according to Y'; and

∿∿ represents the alpha or beta anomer depending on the position of $R_{1'}$;

$R_8$ is selected from H, OR, $NR_{15}R_{16}$, NH—$NHR_{15}$, SH, CN, $N_3$ and halogen; wherein R is selected from H and $(C_1-C_8)$alkyl, and $R_{15}$ and $R_{16}$ are independently selected from H, $(C_1$-$C_8)$alkyl, $(C_1$-$C_8)$alkyl-$(C_5$-$C_{12})$ aryl and —$CHR_{AA}CO_2H$ wherein $R_{AA}$ is a side chain selected from a proteinogenic or non-proteinogenic amino acid;

Y is selected from CH, $CH_2$, $CHCH_3$, $C(CH_3)_2$ and $CCH_3$;

═ represents a single or double bond according to Y; and

∼ represents the alpha or beta anomer depending on the position of $R_1$.

2. The method of treatment according to claim 1, wherein polycythemia is polycythemia vera.

3. The method of treatment according to claim 1, wherein polycythemia is relative polycythemia.

4. The method of treatment according to claim 1, wherein X represents an oxygen.

5. The method of treatment according to claim 1, wherein $R_1$ and $R_6$ are identical and represent hydrogen.

6. The method of treatment according to claim 1, wherein $R_3$ and $R_4$ are identical and represent hydrogen.

7. The method of treatment according to claim 1, wherein $R_2$ and $R_5$ are identical and represent OH.

8. The method of treatment according to claim 1, wherein Y is selected from CH and $CH_2$.

9. The method of treatment according to claim 1, wherein $R_7$ is selected from $P(O)R_9R_{10}$ or

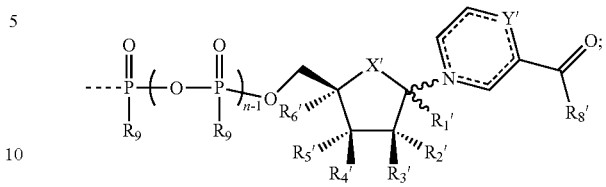

wherein $R_9$ and $R_{10}$ are as described in claim 1 and wherein:
X' is an oxygen;
$R_{1'}$ and $R_{6'}$ each represents a hydrogen;
$R_{2'}$, $R_{3'}$, $R_{4'}$ and $R_{5'}$ are independently selected from hydrogen and OH;
$R_{8'}$ is $NH_2$;
Y' is selected from CH and $CH_2$;
n is equal to 2;
- - - represents the point of attachment;
═ represents a single or double bond depending on Y'; and
∼ represents the alpha or beta anomer depending on the position of $R_{1'}$.

10. The method of treatment according to claim 1, wherein $R_8$ is $NH_2$.

11. The method of treatment according to claim 1, wherein the compound is selected from:

| Compounds (anomers) | Structure |
|---|---|
| 001 (beta) | 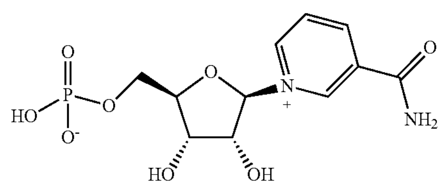 |
| 002 (alpha) | 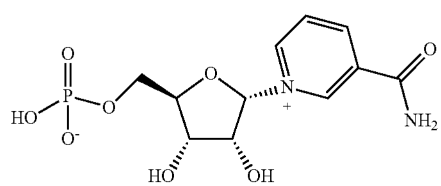 |
| 003 (beta) | 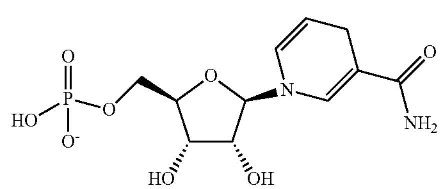 [SMILES: NC(=O)C1=CN([C@@H]2O[C@H](COP(=O)([O-])O)[C@@H](O)[C@H]2O)C=CC1] |
| 004 (alpha) | 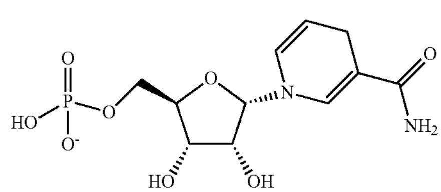 [SMILES: NC(=O)C1=CN([C@H]2O[C@H](COP(=O)([O-])O)[C@@H](O)[C@H]2O)C=CC1] |

| Compounds (anomers) | Structure |
|---|---|
| 009 (beta, beta) | 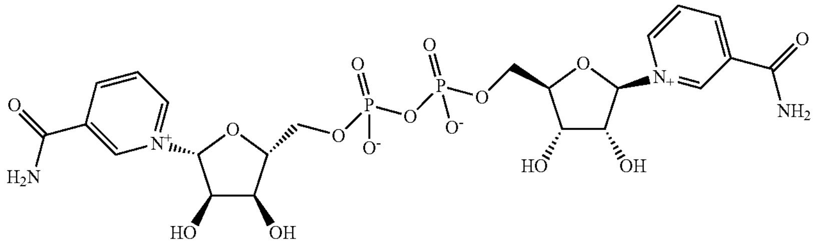 [SMILES: NC(=O)c1ccc[n+]([C@@H]2O[C@H](COP(=O)([O-])OP(=O)([O-])OC[C@H]3O[C@@H]([n+]4cccc(C(N)=O)c4)[C@H](O)[C@@H]3O)[C@@H](O)[C@H]2O)c1] |
| 010 (beta, alpha) | 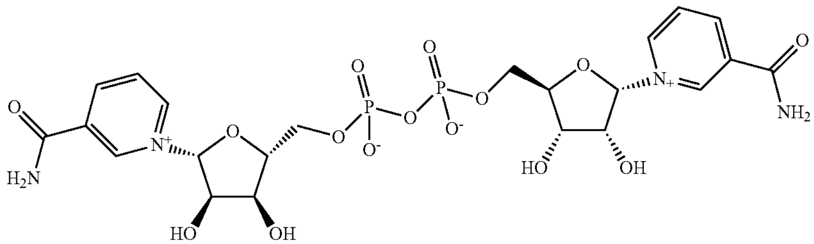 [SMILES: NC(=O)c1ccc[n+]([C@@H]2O[C@H](COP(=O)([O-])OP(=O)([O-])OC[C@H]3O[C@H]([n+]4cccc(C(N)=O)c4)[C@H](O)[C@@H]3O)[C@@H](O)[C@H]2O)c1] |
| 011 (alpha, alpha) | 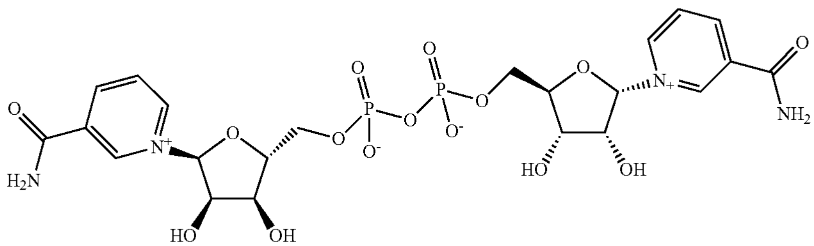 |
| 012 (beta, beta) | 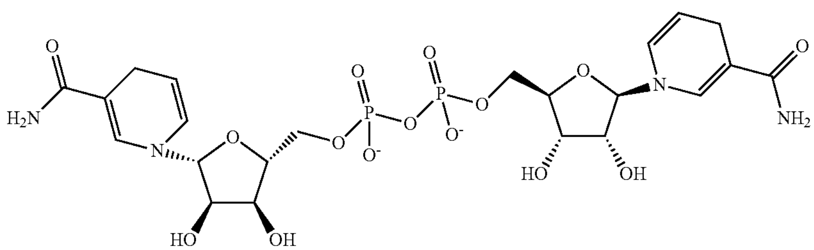 [SMILES: NC(=O)C1=CN([C@@H]2O[C@H](COP(=O)([O-])OP(=O)([O-])OC[C@H]3O[C@@H](N4C=CCC(C(N)=O)=C4)[C@H](O)[C@@H]3O)[C@@H](O)[C@H]2O)C=CC1] |
| 013 (beta, alpha) | 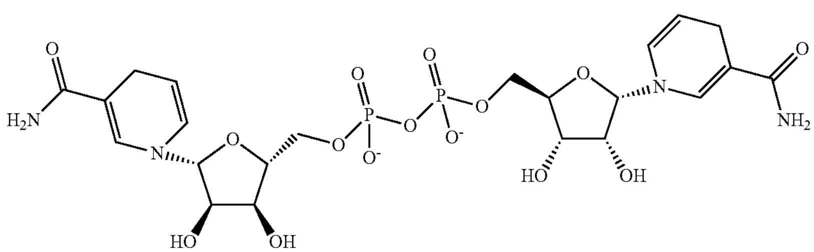 [SMILES: NC(=O)C1=CN([C@@H]2O[C@H](COP(=O)([O-])OP(=O)([O-])OC[C@H]3O[C@H](N4C=CCC(C(N)=O)=C4)[C@H](O)[C@@H]3O)[C@@H](O)[C@H]2O)C=CC1] |
| 014 (alpha, alpha) | | and pharmaceutically acceptable salts and solvates thereof.

12. The method of treatment according to claim 1, wherein the compound is selected from compounds 001, 002, 009, 010 and 011.

13. A method of treatment of polycythemia, the method comprising the administration of a pharmaceutical composition comprising at least one compound according to claim 1 and at least one pharmaceutically acceptable carrier.

14. The method of treatment according to claim 13, wherein polycythemia is polycythemia vera.

15. The method of treatment according to claim 13, wherein polycythemia is relative polycythemia.

16. The method of treatment according to claim 13, wherein the pharmaceutical composition comprises in addition to the at least one compound, at least one other active ingredient selected from: a natural extract; opioid or non-opioid analgesics; NSAIDS; antidepressants; anticonvulsants; antibiotics; CoQ10; PQQ (Pyrroloquinoline quinone); hydroxyurea, L-glutamine, Kynurenine, kynurenic acid, tryptophan, Voxelotor and Crizanlizumab.

* * * * *